United States Patent [19]

Husain et al.

[11] Patent Number: 5,516,647

[45] Date of Patent: May 14, 1996

[54] COMPOUNDS USEFUL AS ALKALINE PHOSPHATASE INHIBITORS AND THERAPEUTIC AGENTS

[75] Inventors: Mazhar Husain, Libertyville; Dominique Bridon, Morton Grove; Mark Bures, Lake Zurich; James D. Ratajczyk, Waukegan; Fortuna Haviv, Deerfield; Christopher Bieniarz, Highland Park, all of Ill.

[73] Assignee: Abbott Laboratories, Abbott Park, Ill.

[21] Appl. No.: 148,142

[22] Filed: Nov. 5, 1993

[51] Int. Cl.⁶ ............................ C12Q 1/42; C07D 513/02
[52] U.S. Cl. .................... 435/21; 435/7.72; 435/7.92; 435/7.93; 435/183; 435/810; 548/154; 514/368; 514/393; 546/271
[58] Field of Search ................ 435/21, 7.92, 7.93, 435/7.72, 183, 810; 548/154, 320; 514/368, 393

[56] References Cited

U.S. PATENT DOCUMENTS

| | | | |
|---|---|---|---|
| 3,364,112 | 1/1968 | Raeymakers | 167/55 |
| 3,817,837 | 6/1974 | Rubenstein | 195/103.5 R |
| 3,852,157 | 12/1974 | Rubenstein | 195/63 |
| 3,852,458 | 12/1974 | Janssen | 424/270 |
| 3,875,011 | 4/1975 | Rubenstein | 195/99 |
| 3,905,871 | 9/1975 | Rubenstein | 195/63 |
| 4,005,212 | 1/1977 | DeBarre | 424/270 |
| 4,090,025 | 5/1978 | Raghu | 548/320 |
| 4,137,321 | 1/1979 | Leeming | 424/270 |
| 4,139,707 | 2/1979 | Raghu | 548/320 |
| 4,143,147 | 3/1979 | Leeming | 424/270 |
| 4,179,460 | 12/1979 | Georgiev | 548/320 |
| 4,310,672 | 1/1982 | Raghu | 548/155 |
| 4,370,482 | 1/1983 | Raghu | 548/155 |
| 4,389,406 | 6/1983 | Dorgan | 424/270 |
| 4,584,305 | 4/1986 | Brugmans | 514/368 |
| 5,093,231 | 3/1992 | Hoke | 435/5 |
| 5,135,847 | 8/1992 | Hoke | 435/5 |
| 5,143,825 | 9/1992 | Chacko | 435/7.9 |
| 5,279,935 | 1/1994 | Nycz | 435/5 |
| 5,284,948 | 2/1994 | Pouticello et al. | 544/295 |

FOREIGN PATENT DOCUMENTS

| | | |
|---|---|---|
| 2340632 | 2/1974 | Denmark . |
| 2340633 | 2/1974 | Denmark . |

OTHER PUBLICATIONS

Biochim. Biophys. Acta, H. Van Belle, *Kinetics and Inhibition of Alkaline Phosphatases from Canine Tissues*, 289 (1972) pp. 158–168.

Proc. Natl. Acad. Sci. USA, J. Berger, et al., *Cloning and sequencing of human intestinal alkaline phosphatase cDNA*, vol. 84, (Feb. 1987) pp. 695–698.

(List continued on next page.)

*Primary Examiner*—David A. Redding
*Assistant Examiner*—Abdel A. Mohamed
*Attorney, Agent, or Firm*—Lawrence S. Pope

[57] ABSTRACT

The present invention discloses novel compounds useful as alkaline phosphatase inhibitors and therapeutic agents. Preferably, the novel compounds are useful as selective inhibitors of human alkaline phosphatases as opposed to *Escherichia coli* alkaline phosphatases. The novel compounds can also be used as cancer therapeutic agents, anti-depressive agents, anti-anergic agents, and antihelminthic agents. The novel compounds have the following general formula:

wherein R' is an aryl, aryl ether, aryl thioether, aromatic heterocyclic, aromatic heterocyclic thioether, or aromatic heterocyclic ether group. More preferably, R' is a phenyl or a pyridine. Most preferably, R' is of the following formula:

2-thiopyridine, or 2-oxypyridine.

$R_1$, $R_2$, $R_3$, $R_4$, $R_1'$, $R_2'$, $R_3'$, $R_4'$, and $R_5'$ can be the same or different, and at least one of which is selected from the group consisting of: H, $C_1$–$C_6$ alkyl, halo $C_1$–$C_6$ alkyl, phenyl, $C_1$–$C_6$ alkoxy, phenoxy, trifluoromethyl, nitro, amino, carboxy, and halo groups with the proviso that each novel compound has no more than three substituents. Hydrogen is not considered a substituent.

34 Claims, 7 Drawing Sheets

OTHER PUBLICATIONS

Journal of Medicinal Chemistry, K. Bhargava, et al., *Tetramisole Analogues as Inhibitors of Alkaline Phosphatase, an Enzyme Involved in the Resistance of Neoplastic Cells to 6–Thiopurines*, vol. 20, No. 4 (1977) pp. 563–566.

Clin. Chem., J. Farley, et al., *Alkaline Phosphatase Activity from Human Osteosarcoma Cell Line SaOS-2: an Isoenzyme Standard for Quantifying Skeletal Alkaline Phosphatase Activity in Serum*, vol. 35, No. 2 (1969) pp. 223–229.

The American Journal of Medicine, W. Fishmann, *Perspectives on Alkaline Phosphatase Isoenzymes*, vol. 56, (May 1974) pp. 617–650.

J. Pharmacol. (Paris), C. Gouret, et al., *Interaction de Divers Psychotropes Avec Cif Effets De L a Réserpine chez la souris et chez le chat*, vol. 8, No. 3 (1977) 333–350.

J. Neurol. Neurosurg. Psychiat., M. Hamilton, *A Rating Scale for Depression*, 23 (1960) pp. 56–62.

Proc. Natl. Acad. Sci. USA, P. Henthorn, et al., *Products of two common alleles at t locus for human placental alkaline phosphatase differ by seven amino acids*, vol. 83 (Aug. 1986) pp. 5597–5601.

Proc. Natl. Acad. Sci. USA, W. Kam, et al., *Cloning, sequencing, and chromosomal localization of human term placental alkaline phosphatase cDNA*, vo. 82 (Dec. 1985) pp. 8715–8719.

The Journal of Biological Chemistry, J. Millan, *Molecular Cloning and Sequence Analysis of Human Placental Alkaline Phosphatase*, vol. 261, No. 7 (Mar. 5, 1966) pp. 3112–3115.

The New England Journal of Medicine, C. Moertel, et al., *Levamisole and Fluoroura for Adjuvant Therapy of Resected Colon Carcinoma*, vol. 322 (Feb. 8, 1990) p. 35 358.

Journal of Immunological Methods, R. Morris, et al., *Cellular Enzyme–Linked Immunospecific Assay (CELISA). IV. Inhibition of Endogenous Cellular Alkaline Phosphatase Activity*, vol. 68 (1984) pp. 11–17.

The Journal of Biological Chemistry, V. Nigam, et al., *Catalysis of Phosphoryl Transfer by Prostatic Acid Phosphatase*, vol. 234, No. 9 (Sep. 1959) pp. 2394–2398.

The Journal of Biological Chemistry, V. Nigam, et al., *Kinetics of Hydrolysis of the Orthophosphate Monoesters of Phenol, p–Nitrophenol, and Glycerol by Human Prostatic Acid Phosphatase\**, vol. 234 (1959) pp. 1550–1554.

The Journal of Histochemistry and Cytochemistry, B. Ponder, et al., *Inhibition of Endogenous Tissue Alkaline Phosphatase with the Use of Alkaline Phosphatase Conjugates in Immunohistochemistry*, vol. 29, No. 8 (1981) pp. 981–984.

Collect. Czech. Chem. Commun., U. Shukla, et al., *Synthesis of trans–2[N–(2 –Hydroxy–1,2,3, 4–Tetrahydronaphthalene–1–YL)]Iminothiazolidine and Related Compounds —a New Class of Antidepressants*, vol. 54 (1992) pp. 415–424.

Proc. Natl. Acad. Sci. USA, M. Weiss, et al., *Isolation and characterization of a CDNA encoding a human liver/bone/kidney–type alkaline phosphatase*, vol. 83 (Oct. 1986) pp. 7182–7186.

COMPOUNDS USEFUL AS ALKALINE PHOSPHATASE INHIBITORS AND THERAPEUTIC AGENTS

FIELD OF THE INVENTION

This invention relates generally to novel compounds useful as inhibitors of alkaline phosphatase. These compounds are useful in immunoassays. They can be used as cancer therapeutics; antihelmintics; anti-depressive/psychoenergising, antianergic, and anti-anorexigenic agents.

DESCRIPTION OF THE BACKGROUND ART

Assay systems which are both rapid and sensitive have been developed to determine the concentration of a substance in a fluid. Immunoassays depend on the binding of an antigen or hapten to a specific antibody and have been particularly useful because they give high levels of specificity and sensitivity. These assays generally employ one of the above reagents in labeled form, the labeled reagent often being referred to as the tracer or detection reagent. Immunoassay procedures may be carried out in solution or on a solid support and may be either heterogeneous, requiring a separation of bound tracer from free (unbound) tracer or homogeneous in which a separation step is not required.

Enzymes have often been used as labels in immunoassays. In a conventional enzyme immunoassay (EIA), an enzyme is covalently conjugated with one component of a specifically binding antigen-antibody pair, and the resulting enzyme conjugate is reacted with a substrate to produce a signal which is detected and measured. The signal may be a color change, detected with the naked eye or by a spectrophotometric technique, or may be conversion of the substrate to a product detected by fluorescence.

The enzymes that are used as labels in an immunoassay must be stable, highly active, available in a highly purified form, yield stable conjugates and be inexpensive, safe and convenient to use. An enzyme which meets these criteria and is extensively used in immunoassays is alkaline phosphatase (hereinafter referred to as "AP"). AP catalyzes the cleavage of phosphate groups from generally colorless phosphorylated substrates to give colored products.

A typical assay is a sandwich immunoassay for detecting an antigen. In this assay, a capture antibody is affixed to a solid support such as a dipstick, membrane, microparticles, microtiter plate well or the inside wall of a tube. The antibody-coated solid support is further coated with an inert protein, such as casein or albumin to block substantially all remaining binding sites on the support and thereby suppress nonspecific binding of tracer directly to the support. Blocking with an inert protein is conventional in the immunoassay art.

A sample solution suspected of containing an antigen is added to the antibody coated and blocked support and conditions conducive to binding the antigen to the antibody are provided. A tracer including a second antibody labeled by covalent conjugation to AP is added. After binding of the second antibody to the antigen, the solid support having affixed thereto an antibody-antigen-labeled antibody bound fraction is contacted with a substrate of AP. The AP substrate is dephosphorylated by the AP component of the bound tracer on the solid support to form a color. The color is indicative of the presence of the antigen and the intensity of the color is directly proportional to the concentration of the antigen in the liquid.

In a typical competitive assay, a limited quantity of the antibody on the solid support may be contacted with the sample and a tracer which includes a known quantity of the antigen having AP conjugated thereto. The antigen and AP-labeled antigen bind to the antibody on the support in direct proportion to their concentrations in the solution. Thus, after binding, the support contains an antibody-antigen bound fraction and an antibody-AP-labeled antigen bound fraction. After separation of the support from the assay solution, the bound fractions on the support may be contacted with the AP substrate to cause formation of a color. However, in the competitive assay of the invention, the color formed is inversely proportional to the concentration of antigen in the liquid.

Endogenous AP is also found in clinical samples and it may interfere with immunoassays using exogenous AP as labels. Typically, in mammals, AP exists in different forms as different isoenzymes. On the basis of tissue specificity, human AP isoenzymes are classified into three types: tissue-nonspecific (found in liver, kidney, bone, spleen, etc.), intestinal, and placental types. These isoenzymes have been well characterized by enzymological and immunochemical approaches {Fishman, W. H. (1974) *Am. J. Med.* 56, 617–650}. Recently, cDNAs for tissue-nonspecific {Weiss, M. J., et al, (1986) *Proc. Natl. Acad. Sic*U.S.A. 83, 7182–7186}, intestinal {Berger, J. et al., (1987) *Proc. Natl. Acad. Sic*U.S.A. 84, 695–698}, and placental {Kam, W., et al., (1985) *Proc. Natl. Acad. Sic*U.S.A. 82, 8715–8719; Millan, J. L. (1986) *J. Bio. Chem.* 261, 3112–3115; Henthorn, P. S., et al., (1986) *Proc. Natl. Acad. Sic*U.S.A. 83, 5597–5601} isoenzymes have been isolated and these have helped in the understanding of the difference and homology in the primary structures of the three isoenzymes.

Phenylalanine and levamisole, (L-)2,3,5,6-tetrahydro-6-phenylimidazo[1,2-b]thiazole, are two well-known inhibitors of AP. The tissue-nonspecific AP are not sensitive to L-phenylalanine, but are strongly inhibited by levamisole; whereas the placental and intestinal isoenzymes are inhibited by both L-phenylalanine and levamisole but only at much higher concentrations.

Advantage has been taken of the above selectivity of the inhibitors in immunoassays (see, e.g., U.S. Pat. No. 5,093, 231). When used in an assay, levamisole does not interfere with the specific immuno-signal generated by calf intestinal AP but does reduce the nonspecific signal which arises from any non-intestinal AP which may be present in a clinical sample. Morris et al., in the *Journal of Immunological Methods* 68, 11 (1984) disclose detection of the binding of monoclonal antibodies to antigens on the surface of whole cells with a conjugate of calf intestinal AP and goat anti-mouse antibodies in the presence of a substrate and levamisole added to inhibit AP of non-intestinal origin.

Ponder et al., (1981) *Journal of Histochemistry and Cytochemistry* 29, 981, disclose detection of mouse H2 antigen in tissue slices by incubating the tissue slices with anti mouse H2 antibody and treating with a calf intestinal AP labeled conjugate followed by a substrate for the enzyme and levamisole to inhibit non intestinal AP. In the Ponder et al. method, levamisole at a concentration of 1 mM is added to a filtered AP substrate solution prior to combining the substrate with the tissue slices.

Levamisole is also used as an antihelminthic drug (U.S. Pat. No. 4,137,321 to Leeming, et al.; U.S. Pat. No. 4,143,147, to Leeming, et al.; U.S. Pat. No. 4,389,406 to Dorgan et al.; U.S. Pat. No. 4,370,482 to Raghu, et al.; U.S. Pat. No. 4,310,672 to Raghu, et al.; U.S. Pat. No. 4,139,707 to Raghu, et al.; and U.S. Pat. No. 4,090,025 to Raghu et al.).

Levamisole has also been used as a nonspecific immunomodulator in the adjuvant treatment of various malignancies (U.S. Pat. No. to 4,584,305 to Brugmans et al.). Levamisole was approved in June 1990 by the United States Drug and Food Administration under the name ERGAMISOL, and is sold by Janssen Pharmaceutical for use in combination with fluorouracil, an already approved drug, for adjuvant treatment of stage C colon cancer after surgical resection.

Levamisole combined with fluorouracil has been associated with one-third reduction in recurrence and risk of death in patients with surgically resected stage C colon cancer as described in C. G. Moertel et al., *New Eng. J. Med.* 322, 352–358 (1990).

Levamisole has also been described as an antidepressive agent (U.S. Pat. No. 3,852,458 to Janssen) and as an antianergic agent (DE 2340633 assigned to Janssen Pharmaceutical). It is also described as possessing psychoenergising and anti-anorexigenic activities, U.S. Pat. No. 4,005,212 to Debarre et al.

SUMMARY OF THE INVENTION

One aspect of the present invention presents novel compounds useful as AP inhibitors. Preferably, the novel compounds inhibit the enzymatic activity of mammalian AP more than non-mammalian AP. More preferably, the novel compounds inhibit human and calf AP more than bacterial AP. The bacterial AP is preferably from *Escherichia coli* (hereafter referred to as "*E. coli*"). The composition for the novel compounds are also presented.

Another aspect of the present invention presents assays using the novel compounds. Preferably, the assays utilize the novel compounds' property as AP inhibitors. More preferably the assays utilize the novel compounds' property as selective inhibitors of mammalian as opposed to non-mammalian AP, and more preferably, human and calf AP as opposed to bacterial AP. The bacterial AP is preferably from *E. coli*. The preferred assays are homogeneous immunoassays, and are more preferably competitive homogeneous assays. The kits for performing such assays are also presented.

Another aspect of the present invention presents the use of the novel compounds as antihelminthic drug, as in veterinary uses.

Another aspect of the present invention presents the use of the novel compounds as antidepressive/psychoenergising, antianergic, and anti-anorexigenic agents.

Another aspect of the present invention presents the use of the novel compounds to treat neoplastic diseases.

DETAILED DESCRIPTION OF THE INVENTION

A. Novel Compounds

Figure 1:
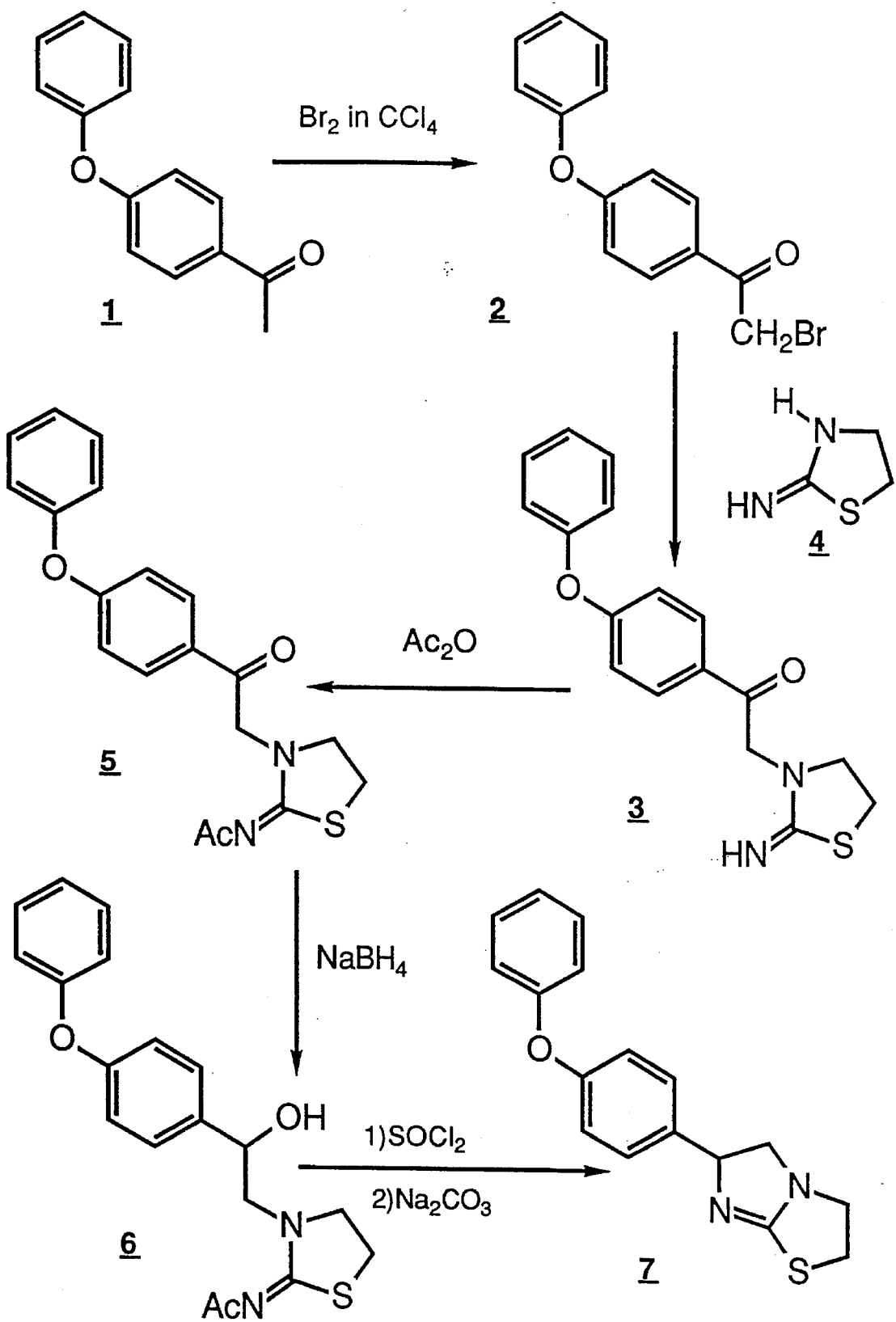
FIG. 1 illustrates the general synthetic pathway for making the novel compound API-1.
Figure 2:
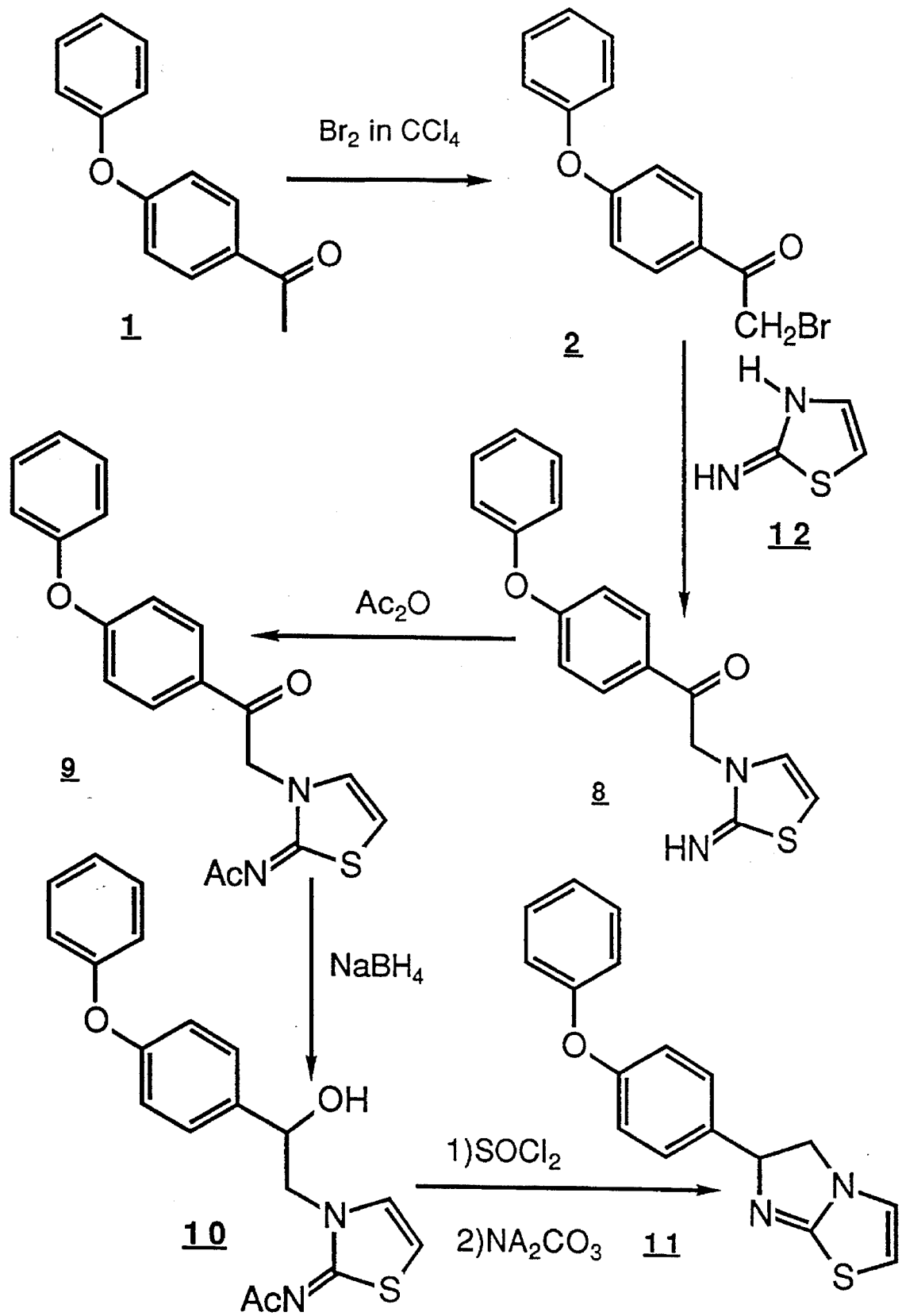
FIG. 2 illustrates the general synthetic pathway for making the novel compound API-2.
Figure 3:
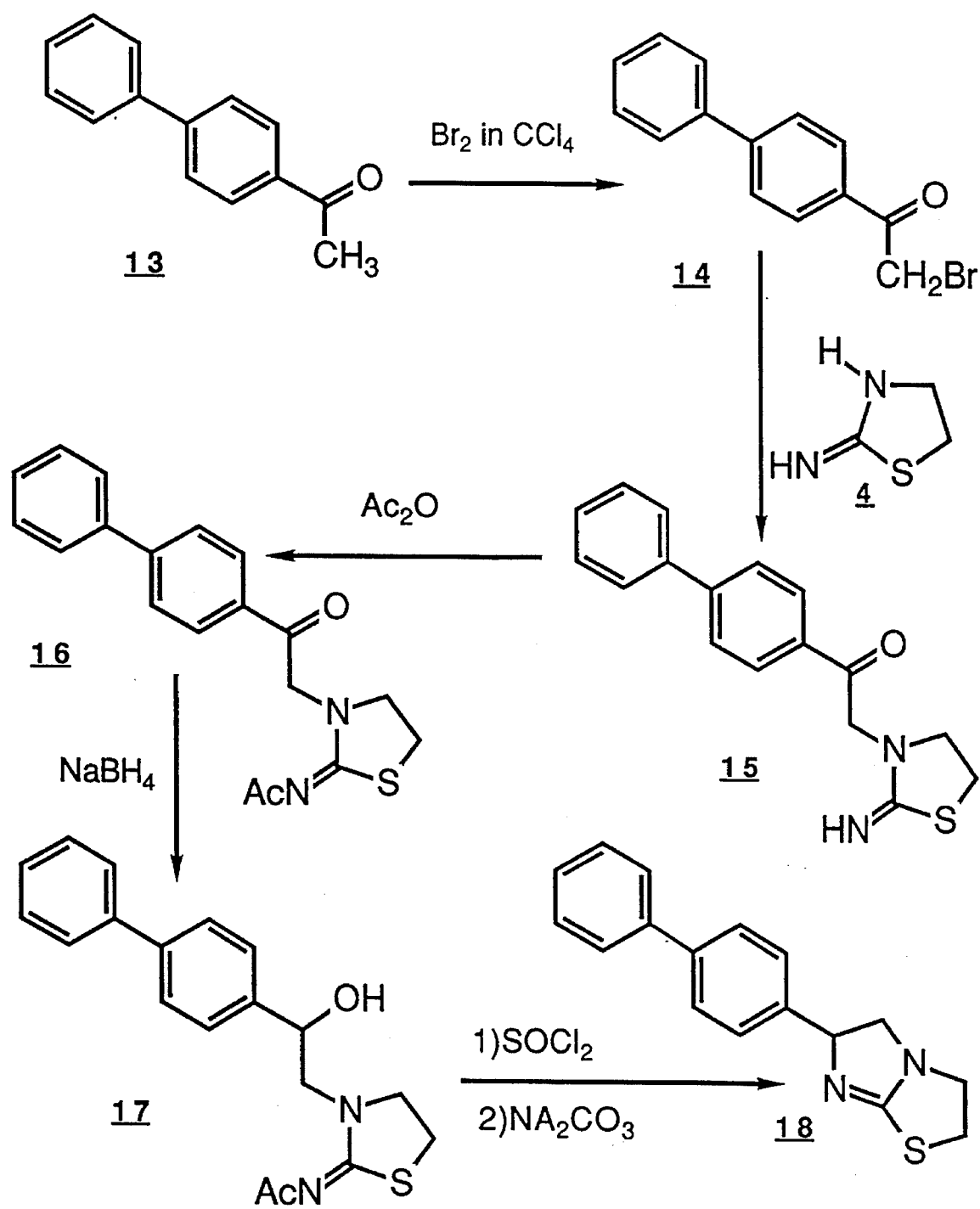
FIG. 3 illustrates the general synthetic pathway for making the novel compound API-3.

The present invention discloses novel compounds selected from the group having the following general formulae:

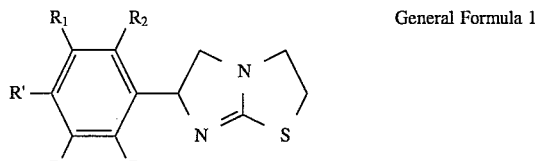

General Formula 1

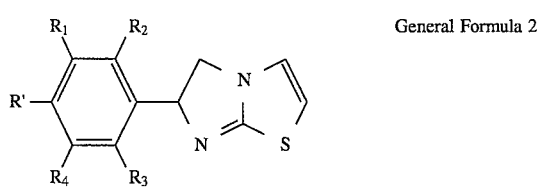

General Formula 2 and the salts of the compounds of General Formulae 1 and 2. In General Formulae 1 and 2, R' is an aryl, aryl ether, aryl thioether, aromatic heterocyclic, aromatic heterocyclic thioether, or aromatic heterocyclic ether group. More preferably, R' is a phenyl or a pyridine. Most preferably, R' is selected from the group consisting of the following formulae:

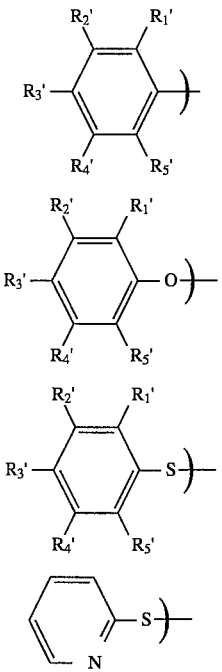

2-thiopyridine, and

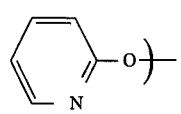

2-oxypyridine.

$R_1$, $R_2$, $R_3$, $R_4$, $R_1'$, $R_2'$, $R_3'$, $R_4'$, and $R_5'$ can be the same or different, and at least one of which is selected from the group consisting of: H, $C_1$–$C_6$ alkyl, halo $C_1$–$C_6$ alkyl, phenyl, $C_1$–$C_6$ alkoxy, phenoxy, trifluoromethyl, nitro, amino, carboxy, and halo groups with the proviso that each novel compound has no more than three substituents. Hydrogen is not considered a substituent. Preferably, at least one of $R_1$, $R_2$, $R_3$, $R_4$, $R_1'$, $R_2'$, $R_3'$, $R_4'$, and $R_5'$ is selected from the group consisting of: $C_1$–$C_4$ alkyl, $C_1$–$C_4$ alkoxy, bromide, chloride, fluoride, phenoxy, phenyl, trifluoromethyl, nitro, primary amine, carboxylic acid, and hydrogen. More preferably, at least one of $R_1$, $R_2$, $R_3$, $R_4$, $R_1'$, $R_2'$, $R_3'$, $R_4'$, and $R_5'$ is selected from the group consisting of: methyl, methoxy, nitro, primary amine, chloride, and hydrogen. Even more preferably, $R_1$, $R_2$, $R_3$, $R_4$, $R_1'$, $R_2'$, $R_3'$, $R_4'$, and $R_5'$ are selected from the the group consisting of: H, $C_1$–$C_6$ alkyl, halo $C_1$–$C_6$ alkyl, phenyl, $C_1$–$C_6$ alkoxy, phenoxy, trifluoromethyl, nitro, amino, carboxy, and halo groups. Further preferred is the case wherein $R_1$, $R_2$, $R_3$, $R_4$, $R_1'$, $R_2'$, $R_3'$, $R_4'$, and $R_5'$ are selected from the the group consisting of: $C_1$–$C_4$ alkyl, $C_1$–$C_4$ alkoxy, bromide, chloride, fluoride, phenoxy, phenyl, trifluoromethyl, nitro, primary amine, carboxylic acid, and hydrogen. Even further preferred is the case wherein $R_1$, $R_2$, $R_3$, $R_4$, $R_1'$, $R_2'$, $R_3'$, $R_4'$, and $R_5'$ are selected from the the group consisting of: methyl, methoxy, nitro, primary amine, chloride, and hydrogen.

Most preferably, all the groups are hydrogen. $R_1$ to $R_4$ and $R_1'$ to $R_5'$ are preferably selected such that these groups do not significantly prevent, e.g. through steric hindrance, the novel compound from binding to and inhibiting the enzymatic activity of AP. Preferably, the novel compounds inhibit mammalian AP more than non-mammalian AP. The mammalian AP is preferably human or calf AP. The non-mammalian AP is preferably bacterial AP which is preferably *E. coli* AP.

One skilled in the art will note that the novel compounds disclosed herein have two isomeric forms: D- and L-. In the Examples, racemic mixtures of D- and L- isomers were used and each racemic mixture is designated "(dl)". Levamisole is an L-isomer and its D- counterpart is not an AP inhibitor. Thus, for inhibiting AP, the L- isomers of the novel compounds are preferred. Since the studies in Example 4 below used the racemic mixtures of the novel compounds, it is postulated that their L-isomers would perform even better as AP inhibitors in the studies. In the synthesis process, the L-isomer can be selected for by means of methods known in the art, such as crystallization, high pressure liquid chromatography, and chiral chromatography.

Since Levamisole, an AP inhibitor, possesses antihelminthic, cancer therapeutic (in particular, in adjuvant treatment of various malignancies), immunomodulating, anti-depressive and anti-anergic properties, it is postulated that the novel compounds which can inhibit AP would have similar properties.

In the following discussion, an Arabic numeral in bold and parenthesis, such as (7), denotes the compound in the Figures with the corresponding bold and underlined Arabic numeral, such as 7.

The most preferred novel compounds are:

(7) (herein also referred to as API-1): (dl)-2,3,5,6-tetrahydro-6-(4-phenoxyphenyl)-imidazo[2,1-b]-thiazole;

(11) (herein also referred to as API-2): (dl)-5,6-dihydro-6-(4-phenoxyphenyl)-imidazo-[1,2-b]-thiazole; and

(18) (herein also referred to as API-3): (dl)-2,3,5,6-tetrahydro-6-(biphenyl)-imidazo-[1,2-b]-thiazole.

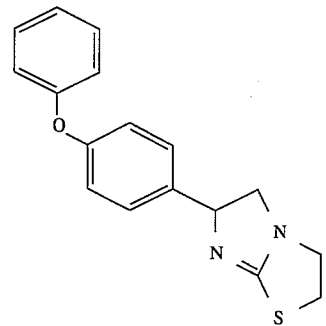

API-1

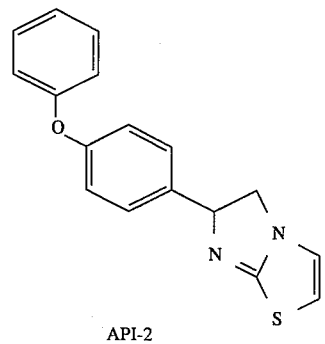

API-2

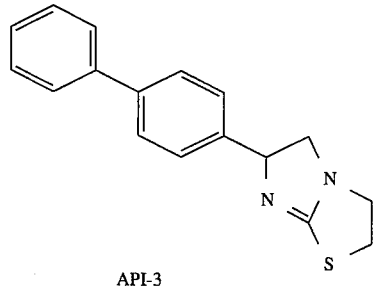

API-3

The novel compounds may be prepared using the same general synthetic pathway. For a specific novel compound, the pathway is modified according to the nature of the substituent on the aromatic ring (or rings) of the novel compound.

In the general synthetic method presented herein, the preparation of API-1, API-2 and API-3 requires seven steps. Aluminum chloride in anhydrous ether and bromine are added to the starting ketone which undergoes an alpha bromination. The resulting alpha-bromoaryl ketone is then reacted with either 2-aminothiazoline or 2-aminothiazole to produce compounds of Structure A or Structure B, respectively.

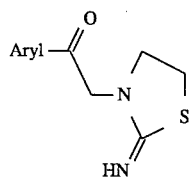

Structure A

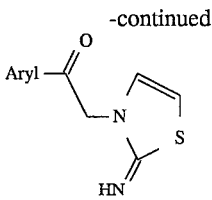

Structure B

Examples of the class of derivatives shown in Structures A and B and their syntheses have been described, for instance, in U.S. Pat. No. 3,364,112 to Raeymakers.

The next step involves the protection of the free amine on either the thiazole or the thiazoline group using techniques known in the art, such as by treating the derivatives with anhydrous sodium acetate in acetic anhydride.

Then, sodium borohydride reduction of the carbonyl group generates the hydroxy intermediates A' and B' of the structures shown below.

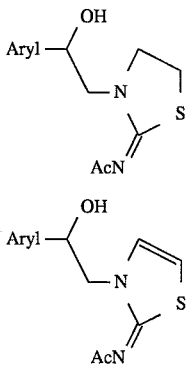

Structure A'

Structure B'

The hydroxy derivative is converted into the chloride by treatment with thionyl chloride. Subsequently, treatment with sodium carbonate causes hydrolysis of the acetyl and cyclization to the bicyclic final compound.

B. The Use of the Novel Compounds in Assays

In contrast with the prior art AP inhibitors, levamisole and L-phenylalanine, the novel compounds are effective over a broad range of mammalian AP isoenzymes. Levamisole is a reasonably potent inhibitor of mammalian AP from several tissue types, but it is approximately 100-fold less potent toward the placental and intestinal isoenzymes. Thus, in the prior art when calf intestinal AP is used as a label in an in vitro assay of sample of mammalian origin, levamisole is used to inhibit the endogenous mammalian non-intestinal AP in the sample.

Compared to levamisole, L-phenylalanine is somewhat more effective against the placental and intestinal isoenzymes. However, L-phenylalanine does not inhibit tissue-nonspecific AP isoenzymes. In fact, the applicants have observed activation of the bone isoenzymes by L-phenylalanine.

Further, the prior art AP inhibitors are not useful in assays using non-mammalian AP such as bacterial AP. Applicants found that when levamisole and L-phenylalanine are used together at high concentrations, they can substantially eliminate endogenous mammalian AP activity, but these conditions also result in the inhibition of non-mammalian AP, such as a 65% inhibition of the altered E. coli AP activity in the case of Levamisole, as shown in Example 4 below. (The altered E. coli AP were those described in "Genetically Engineered Enzymes and Their Conjugates for Diagnostic Assays", to Brate et al., U.S. patent application Ser. No. 08/031,165 filed on Mar. 11, 1993 and its U.S. continuation-in-part patent application of the same title, U.S. patent application Ser. No. 08/100,708 filed on Jul. 29, 1993. These patent applications are hereafter referred to as "U.S. patent Ser. No. 08/031,165 and its CIP". These references are herein incorporated by reference in their entirety). Such inhibition severely compromises the sensitivity of any assay using, for example, E. coli AP.

In summary, the most preferred novel compounds of this invention, API-1 and API-2: (a) are much more potent than levamisole and L-phenylalanine; (b) are effective against all the mammalian isoenzymes; and (c) are more importantly, much more selective in inhibiting mammalian AP isoenzymes as opposed to E. coli AP. The above advantages are demonstrated in the Example 4 below. In view of the above advantages, the inclusion of the novel compounds in assays which use E. coli AP, as enzymatic detection reagent, can effectively overcome the interference from endogenous mammalian AP frequently encountered in clinical samples. The effective inhibition provides for more sensitive assays.

The novel compounds can be used in any situation in which one wishes to preferentially inhibit mammalian AP as opposed to non-mammalian AP. The preferred mammalian AP are human and calf AP. The preferred non-mammalian AP is a bacterial AP such as E. coli AP. Other examples of bacterial AP are the AP from: Serratia marcascens; Saccharomyces cerevisiae, and Bacillus subtilis. "Non-mammalian AP" as used herein include both non-mammalian wild type AP and non-mammalian altered AP. "Bacterial AP" as used herein include both bacterial wild type AP and bacterial altered AP. Alteration of an AP, to form altered AP, can be achieved chemically or recombinantly, as further discussed below.

The novel compounds are useful, for example, in assays of biological samples from mammalian sources wherein non-mammalian AP is used as an enzymatic detection reagent. Endogenous mammalian AP are usually present in mammalian samples and would interfere with the assay. The mammalian samples can be tissue samples but are preferably fluid samples such as blood, serum, plasma, milk, sputum, urine, spinal cord fluid, or fecal extract.

Additionally, since the present novel compounds preferentially suppress non-intestinal AP, they are also useful in assays in which the enzymatic detection reagent is a mammalian intestinal AP and the sample does not contain endogenous mammalian intestinal and placental AP.

Example 4 below discloses that as compared to human intestinal AP, calf intestinal AP is more resistant to inhibition by API-1 and API-2. Thus, in an assay which uses calf intestinal AP as a label, the novel compounds can be used to inhibit endogenous human AP without greatly affecting the performance of the assay.

In general, the immunoassay of the invention may be used to determine any analyte for which i is possible to obtain an anti-analyte which binds substantially specifically to the analyte. Thus, if the analyte is an antigen, a suitable anti-analyte would be a specific antibody. If the analyte is a hapten, a suitable anti-analyte would be an anti-hapten antibody. If the analyte is an antibody, examples of suitable anti-analytes include a specific anti-antibody and the antigen of the antibody. Antibodies useful in the invention as anti-analytes may be either monoclonal or polyclonal. Raising of specifically binding antibodies is well known in the art.

The analyte includes low molecular weight substances, e.g., steroids such as testosterone, progesterone, corticosterone, aldosterone; thyroid hormones such as thyroxine and triiodothyronine; physiologically active peptides, e.g., bradykinin, angiotensin, thyroid hormone-releasing hormone, and luteinizing hormone-releasing hormone; physiologically active amines such as epinephrine, norepinephrine, histamine, and serotonin; prostaglandin; relatively low molecular weight substances, e.g., insulin, glucagon, adrenocorticotropic hormone, and gastrin; and high molecular weight substances, e.g., human chorionic gonadotropin, growth hormone, human placental lactogen, immunoglobulin E, alpha-fetoprotein, hepatitis B antigen. In the case where the analyte is an antigen, examples of the antigen include antigens of micro-organisms such as human immunodeficiency virus (HIV) antigens, tumor-specific antigens, cell or tissue antigens, and serum antigens. The analyte is preferably small molecules such as therapeutic drugs, drugs of abuse, and toxins.

The immunoassay of the invention may be carried out by any conventional sandwich or competitive procedure as known in the art. The assay may be either heterogeneous or homogeneous, and may be carried out in the liquid phase or on a solid support.

1. Use of the Novel Compounds in Assays using Altered AP

One aspect of the invention presents a homogenous, one-step (i.e. no-wash) immunoassay using the novel compounds.

AP is commonly used as an enzymatic detection reagent in a heterogeneous diagnostic assay to assay for analyte such as small molecules in a mammalian sample. The analyte in the sample is caused to bind to a solid support. Such an assay requires a separation step to remove the unbound analyte and the endogenous mammalian AP, if any, before the AP detection reagent is added. The AP detection reagent would then bind the bound analyte to form a complex. When AP substrate is added to the complex, the AP detection reagent would produce a color change. Thus, a heterogeneous assay requires an additional separation step over that of a homogeneous assay.

In one aspect of this invention, the separation step can be obviated by using a non-mammalian altered AP, a binding molecule, and the novel compounds, resulting in a homogenous, one-step immunoassay. The altered AP can be obtained chemically or recombinantly. The AP can be altered, for example, by: (1) selectively mutating the AP using methods such as those described in U.S. patent Ser. No. 08/031,165 and its CIP, hereby incorporated by reference; or (2) by randomly haptenating AP, for example, by using the technology disclosed in U.S. Pat. Nos. 3,852,157; 3,905,871; and 3,817,837, hereby incorporated by reference.

U.S. patent Ser. No. 08/031,165 and its CIP also describe examples of a homogenous, one-step, no wash, competitive immunoassay of samples which uses altered *E. coli* AP. In the assays of mammalian samples, the novel compounds can be used to selectively inhibit any endogenous mammalian AP which may be present and which have much higher specific activities than the altered *E. coli* AP. If uninhibited, these endogenous mammalian AP can severely affect assay performance.

U.S. patent Ser. No. 08/031,165 and its CIP present hybrid enzymes which are examples altered AP. Two types of hybrid enzymes are presented: hybrid enzyme epitope and hybrid enzyme-ligand conjugate. For example, in hybrid enzyme-ligand conjugate, the altered AP has a genetically created site (e.g. which is created the insertion or replacement of amino acid(s) on the AP) which is used to covalently attach a ligand. The ligand in turn binds a binding molecule, and such binding modulates, i.e. either increases or decreases, the enzymatic activity of the altered AP. The analyte competes with the ligand for binding to the binding molecule. AP substrate is added to the sample mixture of the altered AP and binding molecule. The analyte is detected by monitoring the enzymatic activity of the altered AP.

In the case of hybrid enzyme epitope, an epitope for the binding molecule is recombinantly inserted into the AP. The assay using hybrid enzyme epitope is similar to that using hybrid enzyme-ligand conjugate. U.S. patent Ser. No. 08/031,165 and its CIP specifically show examples of altered *E. coli* AP as hybrid enzyme-ligand conjugate and hybrid enzyme epitope. The novel compounds can be used in the above assays to inhibit any mammalian AP which may be present in the assay sample.

As used herein, "ligand" is defined as a chemical group or molecule capable of being bound or conjugated to another chemical group or molecule. Ligands are molecular species that are capable of competing against or inhibiting the binding of the analyte. Such a ligand can be a small molecule or a macromolecule. Examples of ligands include theophylline, antibiotics, peptides, proteins, carbohydrates, lipids and nucleic acids. Preferably, smaller molecular weight oligopeptides which represent or mimic the epitopes of the analytes are used. The ligands are covalently attached to the foreign amino acid moiety which has been genetically inserted into or has replaced an amino acid sequence in the AP via chemical linkers.

As used herein, a "binding molecule" is a molecule which can, through chemical or physical means, specifically bind to the analyte, its analogs, its derivatives, its fragments, a molecule with a binding site in common with the foregoing, the antigenic portions or epitopes of the foregoing (such as in the case where the analyte is an antigen and the binding molecule is an antibody against the antigen). A "binding molecule pair" consists of the binding molecule and the analyte to which it is capable of binding. In addition to antigen and antibody binding molecule pair, other binding molecule pairs include biotin and avidin, carbohydrates and lectins, complementary nucleotide sequences (including probe and captured nucleic acid sequences used in DNA hybridization assays to detect a nucleic acid sequence), effector and receptor molecules, enzyme cofactors and enzymes, enzyme inhibitors and enzymes, and the like.

In one example, the altered AP may be designed such that when the binding molecule is bound to the altered AP, it modifies the latter's enzymatic activity and the signal generated. For example, when the binding molecule binds to the altered AP, it can sterically hinder the AP substrate from interacting with the bound altered AP. Thus, when little or no analyte is present in the reaction mixture, a greater fraction of the binding molecules would bind to the altered AP and less signal would be generated. When analyte is present, the binding molecule and the analyte would interact and thus the active site on the altered AP would be left available. This causes more AP substrates to come into contact with the active site and be converted to AP products, thereby giving more signal. As the concentration of analyte increases, the signal also increases. This generates a curve from which the concentration of the analyte in the test sample can be determined. The amount of attenuation is controlled by the amount of substrate, the amount of binding molecule, the altered enzyme used, and the amount of analyte present.

Other interaction mechanisms and assays are disclosed in U.S. Pat. Ser. No. 08/031,165 and its CIP. These patent applications disclose, for example, hybrid enzyme (i.e. an example of an altered enzyme), such as an "AP-epitope" which has at least one amino acid inserted into or replaced near the active site of the AP to create an epitope for a binding molecule. This epitope and the analyte compete for binding to the binding molecule. When the binding molecule is bound to the epitope, the AP-epitope's enzymatic activity is modified. The changes in the enzymatic activity are dependent upon the presence, or the amount, of the analyte. In another embodiment, such as a hybrid enzyme-ligand conjugate, the altered enzyme consists of a cysteine introduced near the active site of an AP to give an altered enzyme. The cysteine on the altered enzyme serves as a point of conjugation of a ligand, such as theophylline, ferritin, thyroxine, or digoxigenin, to form the hybrid enzyme-ligand conjugate. The ligand and the analyte compete for binding to the binding molecule. When the binding molecule is bound to the ligand, the hybrid enzyme-ligand conjugate's enzymatic activity is modified.

Thus, in an assay for an analyte in a test sample which may contain mammalian alkaline phosphatase, the assay steps may consist of the following: (a) sequentially or simultaneously allowing the test sample, a binding molecule of the analyte, a non-mammalian altered AP, AP substrate, and the novel compound(s) to come into contact; and (b) monitoring changes in the rate of catalysis of the AP substrate by the non-mammalian altered AP, the changes being dependent upon the analyte present in the reaction mixture.

The preferable assay steps are as follows: (1) the test sample and binding molecule are combined and incubated for a sufficient time for the analyte, if present, to bind to the binding molecule; (2) then altered AP is added and the mixture is incubated for a sufficient time for the altered AP and the analyte, if present, to compete for binding to the binding molecule; and (3) AP substrate is added and its catalysis monitored. The novel compound(s) can be added in step (2) or (3).

Alternatively, the assay steps can be as follows: (1) the binding molecule is added to the altered AP and the mixture is incubated for a sufficient time to allow the binding molecule to bind to the altered AP; (2) then the test sample is added and the mixture is incubated for a sufficient time for the altered AP and the analyte, if present, to compete for binding to the binding molecule; and (3) AP substrate is added and its catalysis monitored. The novel compound(s) can be added in step (2) or (3).

In the third alternative: (1) the test sample, altered AP, and binding molecule are combined and incubated for a sufficient time for the altered AP and the analyte, if present, to compete for binding to the binding molecule; and (2) AP substrate is added and its catalysis monitored. The novel compound(s) can be added in step (1) or (2).

The above assays can be calibrated with solutions containing known concentrations of the analyte. Sample of unknowns are run by the assay procedure and their analyte concentrations determined by comparing their signals with a curve determined from the results of the calibrators.

To illustrate the current invention, the following describes in more detail an example of an assay using the altered *E. coli* AP, APKJ3. APKJ3 is an *E. coli* AP wherein the residue Lysine close to the enzyme's active site (at position 167) has been replaced by cysteine by site directed mutagenesis. The resulting AP is further conjugated to the ligand aminomethyltheophylline through the cysteine on the AP, to form APKJ3-Aminomethyl Theophylline Conjugate (also called "T1–3" in U.S. patent Ser. No. 08/031,165 and its CIP which disclose the making of APKJ3 and T1–3, and immunoassays using them). The enzymatic activity of APKJ3-Aminomethyl Theophylline Conjugate decreases when it is bound by an antibody to theophylline. In this case, antibody to theophylline is the binding molecule. APKJ3-Aminomethyl Theophylline Conjugate can thus be used to assay for theophylline in human blood sample.

The following describes an immunoassay for detecting and quantifying theophylline in a human serum sample which can be run on the Cobas Mira instrument ("Mini Random Access" Analyzer, Roche Diagnostic Systems, Inc., Branchburg, N.J.) using APKJ3-Aminomethyl Theophylline Conjugate and Theophylline Polyclonal Sheep Antisera (Catalog #664–43, Abbott Laboratories, Abbott Park, Ill.). The Cobas Mira instrument can utilize either a two reagent or a three reagent configuration when performing assays. The instrument operates with two probes, the reagent probe and the sample probe. The reagent probe picks up Reagent #1 and the sample probe picks up the test sample. Both Reagent #1 and the sample are then dispensed into a cuvette. The reagent probe then picks up Reagent #2 and dispenses it into the cuvette. In a three reagent assay, the reagent probe will also pick up Reagent #3 and dispenses it into the cuvette. The three reagent configuration on the Cobas Mira is as follows:

Reagent #1: 250 µl of PNPP at 5 mg/ml in 0.1M Tris buffer with 1 mM $MgCl_2$, 0.1 mM $ZnCl_2$, 0.5% BSA, and 1.6 mM AP1-1 or 0.4 mM AP1-2 (pH 7.5).

Sample: 2 µl of human serum sample washed with 98 µl of distilled $H_2O$.

Reagent #2: 35 µl of Polyclonal Sheep Antisera at $1 \times 10^{-6}$M washed in 2 µl distilled $H_2O$.

Reagent #3: 10 µl of APKJ3-Aminomethyl Theophylline Conjugate (dissolved in 0.1M Tris buffer with 1 mM $MgCl_2$, 0.1 mM $ZnCl_2$ to an A450 of 0.1) washed with 2 µl of distilled $H_2O$.

A three reagent assay is run on the Cobas Mira instrument as follows:

Reagent #1 is picked up with the reagent probe and then the sample is picked up with the sample probe. Reagent #1 is dispensed into the cuvette followed by the sample. The mixture is then mixed with the reagent probe. The reagent probe then picks up Reagent #2 and dispenses it into the cuvette and mixes the resulting solution. About 20 seconds later, Reagent #3 is picked up by the reagent probe, dispensed into the cuvette and mixed. The whole mixture is then incubated for a total of 4–10 min. The sample is read off the Cobas Mira theophylline calibration curve.

A two reagent assay can be tested on the Cobas Mira instrument as follows:

Reagent #1: 280 µl of PNPP at 5 mg/ml in 0.1M Tris buffer with 1 mM $MgCl_2$, 0.1 mM $ZnCl_2$, 0.5% BSA, 1.6 mM AP1-1 or 0.4 mM AP1-2, and the polyclonal sheep antisera mixture in the same buffer as above.

Sample: 2 µl sample washed with 10 ml Of water.

Reagent #2: 10 µl of APKJ3-Aminomethyl Theophylline Conjugate (dissolved in 0.1M Tris buffer with 1 mM $MgCl_2$, 0.1 mM $ZnCl_2$ to an A450 of 0.1) washed with 2 ml of distilled $H_2O$.

The two reagent assay is performed as described above, except for omitting Reagent #3.

As is shown above, the novel compounds can be used in a clinical chemistry analyzer. Besides Cobas Mira, examples of these analyzers include: the Hitachi 700 and 705 (manufactured by Hitachi Ltd., distributed in the United States by Boehringer Mannhelm Corp., Diagnostic Laboratory Systems Division, Indianapolis, Ind.); the MONARCH PLUS (Instrumentation Laboratory, Lexington, Mass.) and the Spectrum (Abbott Laboratories) instruments.

2. Use of the Novel Compounds in Assays Using Bacterial AP as a Label

Another aspect of the invention presents a heterogenous immunoassay method wherein a sample which may contain mammalian AP is to be assayed for an analyte of interest.

The sample is exposed to a solid support which non-specifically binds the analyte and the mammalian AP such that they cannot be removed from the solid support by washing. The washing merely removes materials which are not bound to the solid support. The novel compounds are used to inhibit the bound mammalian AP, while the detection reagent which is labeled with non-mammalian AP is used to bind and detect the bound analyte.

The solid support can be of any materials so long as they are capable of binding the analyte. For example, the materials for solid support can be any of those used for immunoassays. Natural, synthetic or naturally occurring materials that are synthetically modified can be used. They include: polysaccharides, e.g., cellulose materials including paper, cellulose and cellulose derivatives such as cellulose acetate and nitrocellulose; silica; fiberglass; inorganic materials such as deactivated alumin, diatomaceous earth or other inorganic finely divided material uniformly dispersed in a porous polymer matrix made of polymers such as vinyl chloride, vinyl chloride-propylene copolymer, and vinyl chloride-vinyl acetate copolymer; cloth, both naturally occurring (e.g., cotton) and synthetic (e.g., nylon); porous gels such as silica gel, agarose, dextran and gelatin; polymeric films such as polyacrylamide; magnetic particles; microtiter plates; polystyrene tubes; protein binding membranes; agarose; Sephadex (Pharmacia Fine Chemicals, Inc., Piscataway, N.J.); Trisacryl (Pointet-Girard, France); silicon particles; porous fibrous matrixes etc.

If the analyte is a protein, a preferred solid support is a latex microparticle which binds protein. However, the latex microparticle would also bind other proteins, such as mammalian AP, in the sample. Thus, preferably, the detection reagent is labeled with non-mammalian AP, such as *E. coli* AP, and the novel compounds are used to preferentially inhibit the bound mammalian AP.

The following describes an example of an assay for an analyte in a sample, wherein the sample may contain mammalian AP. The assay steps comprise the following: (a) exposing the sample to a solid support capable of binding the analyte and mammalian AP; (b) incubating the sample and the solid support for a time sufficient for the binding of the analyte to the solid support; (c) removing reagents which are not bound to the solid support; (d) exposing the solid support to a reagent capable of binding to the analyte, the reagent being labeled with non-mammalian AP; (e) incubating the solid support and the reagent for a time sufficient for the binding of the reagent to the bound analyte; (f) removing the reagent which is not bound to the solid support; the removal may be effectuated by washing the solid phase with a buffer solution as is typical of conventional immunoassays; (g) adding the novel compound(s) and an AP substrate to the solid support; and (h) assaying for the presence of the analyte by assaying for the conversion of the AP substrate by the non-mammalian AP into an enzymatic product.

The novel compounds may be used, for example, in an assay for Chlamydia antigen in a human sample which uses anti-Chlamydia immunoglobulin labeled with *E. coli* AP. In this assay, microparticles are incubated with diluted human serum samples. The Chlamydia antigens and endogenous human AP, if present in the samples, are bound to the microparticles. The microparticles are washed and incubated with anti-Chlamydia immunoglobulins labeled with *E. coli* AP. The anti-Chlamydia immunoglobulins will bind any Chlamydia antigens that are bound to the microparticles. The microparticles are again washed. AP substrate, 4-methylumbelliferyl phosphate (4-MUP), and the novel compounds are then added to the microparticles. The novel compounds inhibit any endogenous human AP that may be bound to the microparticles. Any anti-Chlamydia immunoglobulin labeled with *E. coli* AP which is bound to the Chlamydia antigen on the microparticle would convert the nonfluorogenic MUP to 4-methylumbelliferone (MU) whose fluorescence can be measured and related to the presence of Chlamydia antigens in the sample.

C. Compositions; and Concentrations of the Novel Compounds Useful for Immunoassays The novel compounds can be stored dry, in any salt form which can be readily made by reacting each compound with an acid using methods known in the art. Alternatively, the novel compounds may be stored as solution. Any non-toxic acid-addition salt together with a non-toxic diluent or carrier can be used. The novel compound may be stabilized at the alkaline pH required by AP by combining it in a composition which includes selected high pH amine buffers. The buffer of the invention may be any high pH amine buffer in which the novel compound is stable. Suitable buffers are triethanolamine, 2-amino-2-methyl-1,3-propanediol (AMPD) and, preferably, 2-amino-2-methyl-1-propanol (AMP). The amine may be present in the buffer at a concentration of about 1–100 millimolar, and preferably about 40–60 millimolar. The most preferred buffer is 50 mM AMP, pH 9.8. The composition may include the buffer, one or more of the novel compounds, the substrate for AP, and optionally magnesium chloride.

Since the novel compounds are more effective at suppressing mammalian AP than levamisole and L-phenylalanine, they can be used at a lower concentration. Additionally, in the prior art, levamisole and L-phenylalanine are used in combination because levamisole is more effective against tissue-nonspecific AP whereas L-phenylalanine is more effective against tissue specific AP. Though the novel compounds can be used singularly or in combination, they are effective against both tissue-nonspecific AP and tissue specific AP at concentrations lower than those used for levamisole and L-phenylalanine. Thus, the novel compounds can be used singularly, unlike the prior art inhibitors. The concentration of the novel compounds in the compositions may be optimized by one skilled in the art for *E. coli* AP and other AP, for example, using the method shown in Example 4 and its Table 1 described below.

Suitable substrates for AP which may be included in the composition are phosphate esters of a nitrophenol, preferably p-nitrophenol. Preferred substrates are phosphate esters of 3-hydroxyindoles which, upon dephosphorylation, undergo oxidative coupling to colored indoxyls. Exemplary of such substrates are 5-bromo-4-chloro-3-indolyl phosphate, and preferably, 3-indolyl phosphate. The substrate may be present in the composition in a concentration of about 0.1 to 100 millimolar, preferably about 1 to 50 millimolar.

Preferred AP compositions additionally contain magnesium chloride in a concentration of about 0.1 to 2.0 millimolar, preferably about 0.5 to 1.0 millimolar.

D. Assay Kits Containing the Novel Compounds

The composition of the invention may be included as part of a kit useful for performing an assay, preferably an immunoassay, for an analyte. The reagents included in the kit may contain the novel compound(s), a buffer, a substrate for AP and optionally may contain magnesium chloride. Additionally, for a homogenous assay, the kit may contain the non-mammalian altered AP and binding molecules. For a heterogeneous assay where a wash step is involved, the kit may contain the non-mammalian AP labeled detection reagent, a solid phase for attachment of the analyte, and a wash solution for the wash step.

The kit may additionally include containers for the assay reagents and implements, such as vials, droppers and the like useful in performing an assay. The reagents may be contained in separate containers. Some of the reagents may be contained in the same containers if permitted by the assay and their chemistry. For example, in a kit for a homogenous assay, the novel compounds may be contained in the same container as the AP substrate, binding molecule, or the non-mammalian altered AP. Alternatively, the binding molecule may be stored in the same container as the novel compound and/or the non-mammalian altered AP. For a heterogeneous assay where a wash step is involved, the kit may have a container containing both the AP substrate and the novel compounds.

E. The Novel Compounds as Antihelmintics

The novel compounds can also be used as antihelmintic.

A novel compound alone or in combination with another novel compound, e.g. AP1-1 in combination with AP1-2, can be administered alone, but will generally be administered in admixture with a non-toxic diluent or carrier selected with regard to the intended route of administration. For example, they may be administered orally as aqueous solutions or in admixture with an animal feedstuff or animal feed supplement. In parenteral administration, which is preferably carried out subcutaneously or intramuscularly, the carrier may be aqueous such as water or isotonic saline or non-aqueous such as polyethylene glycol 300. The pharmaceutically acceptable acid addition salts may be prepared from the corresponding free base by conventional procedures.

It will be noted that the effective dosage of the compounds will differ depending on the animals and the worms involved. The dosage can be determined or adjusted using methods known in the art. For example, the activity and dosage of the compound can be determined in a triple infection mouse screen against concurrent infection of *Nernatospiroides dubius, Syphacia obvelata* and *Hymenolepsis nana* as described in Example 9 of U.S. Pat. No. 4,137,321 to Leeming et al.

The composition may be prepared by mixing the ingredients together, and may be administered in one or more doses. Obviously the amount of the active ingredient will vary according to the dose response and weight of the animal. The compounds of the invention can be active against nematodes occurring in the lungs, stomachs and intestines of sheep, cattle and other domestic animals.

Other routes and forms of administration and compositions can be further found in the following section: "*F. The Novel Compounds a Cancer Therapeutics*" and "*G. The Use of the Novel Compounds as Anti-Depressive, Psychoenergising, Anti-Anergic, and Anti-Anorexigenic Drugs*".

F. The Novel Compounds s as Cancer Therapeutics

The novel compounds disclosed herein can be used to treat neoplastic diseases, thereby aiding in their regression or palliation. Neoplastic disease, as used herein, is meant to include all types of cancerous growths or oncogenic processes, metastatic tissues or malignantly transformed cells, tissues, or organs, irrespective of histophathologic type or stage of invasiveness. For example, the novel compounds may be used in accordance with this invention against such neoplastic disorders as "Lewis Lung 3:", tumor and pulmonary metastases, breast cancer, lung cancer, melanoma, colorectal cancer, multiple myeloma, sarcoma, colon cancer, Maloney leukemia, sarcoma 180 and post operative treatment of malignancies such as colon cancer. The novel compounds can also be combined with other cancer therapeutics, such as fluorouracil, for treatment of neoplastic disease and to reduce the recurrence and risk of death in patients with surgically resected cancer such as stage C colon cancer.

One aspect of this invention comprises systemically administering to subjects hosting neoplastic disease an effective ameliorating amount of the novel compound(s) or a therapeutically active acid addition salt thereof preferably admixed with a pharmaceutically acceptable carrier. Such carrier may take a wide variety of forms depending on the form of preparation desired for administration, i.e., oral or parenteral. In preparing the compositions in oral dosage form, any of the usual pharmaceutical media may be employed, such as, for example, water, glycols, oils, alcohols, and the like in the case of oral liquid preparations such as suspensions, elixirs and solutions or solid carriers such as starches, sugars, kaolin, lubricants, binders, disintegrating agents and the like in the case of powders, capsules and tablets. Because of their ease in administration, tablets and capsules represent the most advantageous oral dosage form, in which case solid pharmaceutical carriers are obviously employed. For parenteral injection, the carrier will usually comprise sterile water, at least in large part, though other ingredients, for example, to aid solubility may be included. Injectable solutions, for example may be prepared in which the carrier comprises saline solution, glucose solution or a mixture of saline and glucose solution. Injectable suspensions may also be prepared in which case appropriate liquid carriers, suspending agents and the like may be employed.

It is especially advantageous to formulate the aforementioned pharmaceutical compositions in dosage unit form for ease of administration and uniformity of dosage. Dosage unit form, as used herein, refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonfuls, tablespoonfuls and the like, and segregated multiples thereof.

The dosage of the principal active ingredient (novel compounds) for the treatment of the particular neoplastic disease may depend on the species and size of the subject being treated; the particular condition and its severity; the particular form of the active ingredient (e.g., soluble salt or less soluble base) and the route of administration.

Regression and palliation of neoplastic disease are aided by the internal administration of novel compounds, preferably as the hydrochloride salt of enantiomorph, and pharmaceutical compositions containing same.

As a dosage regimen, the amount of principal active ingredient administered is a sufficient amount to aid regression and palliation of the neoplastic disease in the absence of excessive deleterious side effects of a cytotoxic nature to the host harboring the disease. The compound(s) may be administered daily to humans for about 3 to 5 days repeated every 2–3 weeks. Alternatively, the compound(s) may be administered over a long period of time, for example 3–6 months.

The strategy used in treating a particular individual depends on the status of the individual and the objective of the treatment. The dosage varies with such factors as the size and age of the individual, stage of the disease, the concurrent treatments being given, e.g. radiotherapy, and the particular novel compound used. In any treatment, the novel compounds must be administered to individuals in a manner capable of getting an effective dose into the blood stream.

The novel compound(s) is administered by any suitable route including oral, rectal, nasal, topical (including buccal and sublingual), vaginal and parenteral (including subcutaneous, intramuscular, intravenous, intra-arterial and intradermal). Examples are intravenous injection and desirable blood levels may be maintained by a continuous infusion or by intermittent infusions. It will be appreciated that the preferred route may vary based on the factors discussed in the previous paragraph.

The novel compounds may be used in therapy in conjunction with other medicaments or radiotherapy. The novel compounds may be presented as part of a pharmaceutical formulation. The formulations of the present invention comprise at least one administered ingredient, i.e. the novel compound(s), together with one or more acceptable carriers thereof and optionally other therapeutic ingredients. The carrier(s) must be "acceptable" in the sense of being compatible with the other ingredients of the formulation and not deleterious to the recipient. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The following is an example of the procedure: the patient is administered the compound(s) intravenously. The tumor cells can also be concurrently killed by chemotherapy and/or radiotherapy. At the end of a five-day period, the patient is evaluated. The evaluation includes physical examination and extensive laboratory testing. The tests include evaluation for toxicity and specific tests directed to the particular tumor involved. For example, in the case of leukemia, the test include determination of white blood cell count. If the patient's condition is stable, he is re-treated at the same dosage twice per week and evaluated weekly. Provided the patient's condition is stable, the treatment is continued for five months. At the end of the five month period, the patient is again evaluated and if appropriate to the disease, X-rayed. Comparison of the pre-treatment and post-treatment X-ray photographs indicate the efficacy of the combined treatments by showing whether the disease has worsened, stabilized or improved, e.g. whether a tumor has grown further or reduced in size. According to the efficacy of the combined treatments, and the patient's condition, the novel compound(s) dosage, the chemotherapy and/or radiotherapy may be increased or maintained constant for the duration of treatment. The patient's condition and the status of the disease is monitored periodically through physical exam, laboratory test and X-ray. The starting dose of novel compound(s), chemotherapy and/or radiotherapy is reduced for a patient who exhibits adverse reaction.

The formulations of this invention may include other agents conventional in the art having regards to the type of formulation in question. Further, the above treatment methods are by way of example, and do not preclude those known by persons skilled in the art. For example, other routes and forms of administration and compositions can be further found in the following section.

G. The Use of the Novel Compounds as Anti-Depressive, Psychoenergising, Anti-Anergic, and Anti-Anorexigenic Drugs The novel compounds can also be used as anti-depressive, psychoenergising, anti-anergic, and anti-anorexigenic drugs. The following will discuss the use of the novel compounds as anti-depressive, though the discussion can be similarly applied to the other uses mentioned in this paragraph.

The novel compounds can be used to inhibit depression when administered to a depressed mammal, particularly humans, alone or as a therapeutically active, non-toxic, acid addition salt thereof. Preferably, the active ingredient is intimately admixed with a pharmaceutically acceptable carrier in dosage unit forms for ease of administration and uniformity of dosage, each unitary dosage containing a predetermined quantity of active ingredient calculated to produce the desired therapeutic carrier.

The dosage for the novel compounds to achieve antidepressant activity can be determined using standard methods known in the art. For example, they can be determined from clinical studies in human beings, such as depressed psychotic patients, for their effects on depression and mental concentration. Depression can be assessed on the Hamilton Scale [(1960) *J. Neurol Neurosurg*, Psychiat. 23, 56].

The antidepressive activity of the novel compound can also be determined by testing it for antagonism towards the ptosis caused by reserpine (C. Gouret et. al., (1977) *J. Pharmacol.* (Paris) 8, 333–350). For example, test mice can be simultaneously administered with the novel compounds in solution (through intraperitoneal administration) and reserpine (through subcutaneous administration). After sixty minutes, the degree of palperbral ptosis is estimated for each mouse by means of a rating scale. The average rating and the percentage variation, relative to the control mice, are calculated for each dose. The $AS_{50}$, or the dose which reduces the average ptosis score by 50%, relative to the control animals, is determined graphically for each compound and the effective dose determined therefrom. The efficacy and dosage for the compounds can also be determined by the methods discussed, for example, in U. K. Shukla (1992)*Collect. Czech. Chem. Commun.* 57, 415–424 and U.S. Pat. No. 4,005,212, to Debarre et al.

Further, the effect of the compounds on mental concentration of a test subject can be assessed by means of the Gr ünbaun dynamic concentration test [Rutten, J. W. H. M., *Attentiviteit als Psychodiagnosticum*, Swets and Zeitlinger, Amsterdam, 1964] in which the patients has to arrange randomly given numbers in an increasing or decreasing sequence; their reaction time is measured by making the patient put in a key as a response to a light going on. Typical clinical studies are described in U.S. Pat. No. 3,852,458, to Janssen.

The compounds may be prepared as a pharmaceutical compositions. To prepare an example of the pharmaceutical compositions of this invention, the novel compounds in base or acid-addition salt form can be combined in intimate admixture with a pharmaceutically acceptable carrier, which carrier may take a wide variety of forms depending on the forms of preparation desired for administration. These pharmaceutical compositions are desirable in unitary dosage form suitable, preferably, for administration orally, rectally or by parenteral injection. For example, in preparing the compositions in oral dosage forms, any of the usual pharmaceutical media may be employed, such as for example, water glycols, oils, alcohols and the like in the case of oral liquid preparations such as suspensions, syrups, elixirs and solutions, or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions the carrier will usually comprise saline solution, glucose solution or a mixture or saline and glucose solution. Injectable suspensions may also be prepared in which case appropriate liquid carriers, suspending agents and the like may be employed. Acid addition salts of the novel compound, due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form herein refers to physically discrete units suitable as unitary dosage, each unit containing a predetermined quantity of active ingredient calculated to produced the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The formulations of this invention may include other agents conventional in the art having regards to the type of formulation in question. Further, the above treatment methods are by way of example, and do not preclude those known by persons skilled in the art. For example, other routes and forms of administration and compositions can be further found in the above section on using the compounds as cancer therapeutics.

The following illustrate the invention and are not to be construed as limiting the invention.

EXAMPLES

Example 1

Synthesis of Compound AP1-1

Preparation of compound (2):

4'-phenoxyacetophenone (1) (42.4 g; 0.20 mol) was stirred at 5° C. in 250 mL of dried ethyl ether. Aluminum chloride (0.2 g; 1.5 mmol) was then slowly added to the solution. Bromine (32.0 g; 0.20 mol; 10.3 mL) was then dropped into the vortexing solution. After 30 minutes at 5° C., the solution was warmed up to room temperature for 12 hours. The volume was then reduced to 100 mL and the organic phase washed with 2 times 100 mL of concentrated sodium bicarbonate in water. Organic phase was then washed with 100 mL of water, dried and concentrated in vacuum to yield 55.0 g of oil (94.5%). MS m/z: 291 ($M^+$). NMR $^1H$ (DMSOD-D6) δ: 4.88 (2H, s); 7.01 to 8.08 (9H, broad m).

Preparation of compound (3):

Bromomethyl 4'-phenoxyphenyl ketone (55 g; 0.189 mol) was dissolved in 400 mL of acetonitrile and 2-amino-2-thiazoline (4) (20.0 g; 0.196 mol) was added rapidly with strong vortex. After 5 minutes at room temperature, the formation of an important amount of precipitate was recorded. After 2 hours the precipitate was collected, rinsed with 3 times 50 mL of acetonitrile, and dried under vacuum. (yield 71%). MS m/z: 313 ($M^+$). NMR $^1H$ (DMSO-D6) δ: 3.58 (2H, t, J=7 Hz); 4.01 (2H, t, J=7 Hz); 5.26 (2H, s); 7.12 (4H, m); 7.28 (1H, t); 7.49 (2H,t); 8.01 (2H, d).

Preparation of compound (5):

Compound (3) (53.0 g; 0.135 mol) was stirred with very strong vortex in 300 mL of acetic anhydride. Anhydrous sodium acetate (13.0 g; 0.158 mol) was then rapidly added. Reaction mixture was left overnight at 80° C. with strong stirring. Precipitate was collected and dissolved with hot isopropanol and water (90/10). All liquid phases were gathered and concentrated to dryness. Residue was then dissolved in methylene chloride and washed with sodium bicarbonate solution and water. Methylene chloride was then concentrated in vacuum and residue redissolved in 10 mL of acetyl acetate. Trituration with petroleum ether gave yellow crystals (45.2 g). Yield 94.8%. MS m/z: 355($M^+$). NMR $^1H$ (DMSO-D6) δ: 1.94 (3H, s); 3.19 (2H, t); 3.72 (2H, t); 5.15 (2H, s); 7.10 (4H, m); 7.28 (1H, t); 7.48 (2H, t); 8.05 (2H, d).

Preparation of compound (6):

Compound (5) (42.4 g; 0.12 mol) was dissolved at room temperature in 250 mL of methanol. Sodium borohydride (6.0 g; 0.158 mol) was then added via spatula, and the mixture was stirred for 1 hour at room temperature. 50 mL of water were added and the mixture was concentrated to dryness in vacuum. The residue was extracted with water/methylene chloride. The organic phase was then dried and concentrated to give 32.0 g of crystals (75%). MS m/z: 357 ($M^+$). NMR $^1H$ (DMSO-D6) δ: 2.01 (3H, s); 3.04 (2H, m); 3.55 to 3.83 (4H, m); 4.91 (1H, m); 5.63 (1H, OH, m); 6.99 to 7.40 (9H, broad m)

Preparation of (dl)-2,3,5,6-tetrahydro-6-(4-phenoxyphenyl)-imidazo[2,1-b]-thiazole (7):

Compound (6) (15.0 g; 42 mmol) was dissolved in 250 mL of methylene chloride and 7 mL of thionyl chloride were added with strong vortex at room temperature. For 15 minutes gas evolution was recorded. A solution made of 24 g of sodium carbonate in 240 mL of water was added and the mixture was refluxed at 65° C. for one hour. The mixture was cooled down to room temperature and the organic phase was extracted with 100 mL of water and 100 mL of methylene chloride. The organic phase was then washed 4 times with a 15% solution of hydrochloric acid in water. Acidic phases were collected and brought to basic pH using ammonia in water. Basic solution were then extracted with 3 times 100 mL of methylene chloride. Organic phase was then dried and concentrated in vacuum. Residue was dissolved in 200 proof ethanol. Acetone was added and 5% hydrochloric acid in water to give 9.4 g of hydrochloride salt of compound (7) (yield 67%). MS m/z: 297 ($M^+$). NMR $^1H$ (DMSO-D6) δ: 3.68 (1H, m); 3.80 (2H, m); 4.00 (2H, t); 4.22 (1H, t); 5.74 (1H, t); 7.01 to 7.10 (4H, m); 7.18 (1 H, m); 7.39 to 7.52 (4H, m). For the last step, hydrochloric acid could be substituted with methanesulfonic acid. In this case, the methanesulfonate salt of compound (7) is obtained.

Example 2

Synthesis of Compound AP1-2

Preparation of compound (8):

Compound (2) (3.13 g; 10.75 mmol) was dissolved in 50 mL of acetonitrile at room temperature. 2-Aminothiazole (12) (1.08 g; 10.79 mmol) was then added and the mixture was stirred with strong vortex for three hours. Precipitate was then filtrated and washed with acetonitrile and ether. Precipitate was dried in vacuum to give 2.65 g of compound (8) (79 %). MS m/z: 357 ($M^+$). NMR $^1H$ (DMSO-D6) δ: 5.79 (2H, s); 7.06 (1H, d, J=6 Hz); 7.15 (4H, m); 7.29 (1H, m); 7.33 (1H, d, J=6 Hz); 7.50 (2H, t); 8.05 (2H, d); 9.60 (1H, s)

Preparation of compound (9):

Compound (8) (1.0 g; 3.22 mmol) was added to 20 mL of acetic anhydride with strong vortex. Anhydrous sodium acetate (0.3 g; 3.80 mmol) was added and the mixture was refluxed at 80° C. overnight. Solution was then concentrated to dryness and the residue was dissolved in methylene chloride. Organic phase was then washed with 10% solution of sodium bicarbonate in water, dried and concentrated in vacuum to give an oil (1.10 g; 97%). MS m/z: 353 (M$^+$). NMR $^1$H (DMSO-D6) δ: 2.01 (3H, s); 5.76 (2H, s); 6.98 (1H, d, J=6 Hz); 7.15 (4H, m); 7.28 (1H, t); 7.42 (2H, d, J=6 Hz); 7.49 (2H, t); 8.12 (2H, m).

Preparation of compound (10)

Compound (9) (1.0 g; 2.82 mmol) was dissolved in 30 mL of methanol and sodium borohydride (0.14 g; 3.68 mmol) was added rapidly to the vortexing solution. The mixture was stirred for 1 hour at room temperature. 10 mL of water were added and the solution was concentrated in vacuum. The residue was then extracted with 50 mL of methylene chloride and 50 mL of water. Organic solution was then dried on magnesium sulfate and concentrated in vacuum to give white crystals of compound (10) (0.92 g; 2.58 mmol). Yield 91.5%. MS m/z: 355 (M$^+$). NMR $^1$H (DMSO-D6) δ: 2.12 (3H, s); 4.28 (2H, m); 5.04 (1H, m); 5.80 (1H, OH, d); 6.88 (1H, d, J=6 Hz); 6.99 (4H, m); 7.14 (1H, t); 7.36 (1H, d, J=6 Hz); 7.39 (4H, m).

Preparation of (dl)-5,6-dihydro-6-(4-phenoxyphenyl)-imidazo-[1,2-b]-thiazole (11):

Compound (10) (220 mg; 0.62 mmol) was dissolved in 10 mL of methylene chloride and 1 mL of thionyl chloride was added with strong vortex at room temperature. After 15 minutes, a solution made of 1.0 g of sodium carbonate in 10 mL of water was added. The mixture was refluxed for one hour at 65° C. The mixture was cooled down to room temperature and 20 mL of water and 20 mL of methylene chloride were added. The organic phase was extracted and washed with 3 times 20 mL of hydrochloric acid 10% in water. The acidic fractions were collected and brought to basic pH using ammonia. Product was extracted using methylene chloride. The organic phase was then dried using sodium sulfate and concentrated to yield a solid. This solid was then dissolved in acetone and a precipitate was obtained by addition of a 5% solution of hydrochloric acid in water. Precipitate was collected to yield 70 mg of white crystals (38%). MS m/z: 295 (M$^+$). NMR $^1$H (DMSO-D6) δ: 4.26 (1H, m); 4.81 (1H, m); 5.80 (1H, m); 7.02 (4H, m); 7.07 (1H, d, J=6 Hz); 7.19 (1H, t); 7.40 (2H, m); 7.50 (1H, m); J=6 Hz); 7.53 (2H, d).

Example 3

Synthesis of Compound AP1-3

Preparation of compound (14)

4-Acetylbiphenyl (13) (3.85 g; 19.62 mmol) was stirred in 60 mL of ethyl ether and 10 mL of methylene chloride. 30 mg of aluminum chloride were added at 5° C. (ice bath). Reaction is very exothermic. Bromine (3.3 g; 20.65 mmol; 1.1 mL) was slowly dropped in the solution. After 1 hour a white precipitate (2.15 g) was collected and the filtrate was extracted with 100 mL of water and 100 mL of methylene chloride. Organic phase was then washed with sodium carbonate, water, then dried and concentrated in vacuum to give another 2.80 g of crystals. Total weight: 4.95 g (92%). MS m/z: 275 (M$^+$). NMR $^1$H (CDCl$_3$) δ: 4.49 (2H, s); 7.48 (3H, m); 7.62 (2H, d); 7.72 (2H, d); 8.05 (2H, d).

Preparation of compound (15)

Compound (14) (4.85 g; 17.64 mmol) was dissolved in 150 mL of acetonitrile. 2-amino-2-thiazoline (4) (2.3 g; 22.55 mmol) was added at room temperature with strong vortex. After 30 minutes a white precipitate from the reaction mixture was collected and washed with acetonitrile and ethyl ether. 4.60 g of product (88%) was collected. MS m/z: 297 (M$^+$). NMR $^1$H (DMSO-D6) δ: 3.59 (2H, t); 4.02 (2H, t); 5.32 (2H, s); 7.46 (1H, d); 7.52 (2H, t); 7.78 (2H, t); 7.92 (2H, d); 8.08 (2H, d)

Preparation of compound (16)

Compound (15) (4.3 g; 14.53 mmol) was stirred with strong vortex in 50 mL of dry acetic anhydride. Anhydrous sodium acetate (1.31 g; 16.00 mmol) was added and the mixture was stirred overnight at 80° C. The mixture was cooled down to room temperature. The precipitate was filtered and redissolved in hot isopropanol. The product (1.53 g) crystallized from the solution. Mother liquor were concentrated to dryness and extracted with water and methylene chloride to yield after concentration another 2.45 g of crystals. Total weight is 3.98 g (81%). MS m/z: 338 (M$^+$). NMR $^1$H (DMSO-D6) δ: 1.96 (3H, s); 3.21 (2H, t); 3.74 (2H, t); 5.21 (2:H, s); 7.46 (1H, d); 7.52 (2H, t); 7.78 (2H, d); 7.89 (2H, d); 8.11 (2H, d).

Preparation of compound (17)

Compound (16) (1.53 g; 4.53 mmol) was dissolved at room temperature in 30 mL of methanol. Sodium borohydride (large excess) was then added and the reaction mixture was stirred for one hour. 30 mL of water were added and the mixture was concentrated to dryness. The residue was dissolved in 50 mL of methylene chloride and washed with 2 times 50 mL of water. The organic phase was dried and concentrated in vacuum to give a white product (1.40 g; 91%). MS m/z: 340 (M$^+$). NMR $^1$H (DMSO-D6) δ: 2.05 (3H, s); 3.08 (2H, m); 3.62 (2H, m); 3.80 (2H, m); 4.96 (1H, m); 5.75 (1H, OH, m); 7.38 (1H, d); 7.48 (4H, m); 7.66 (4H, m).

Preparation of (dl)-2,3,5,6-tetrahydro-6-(biphenyl)-imidazo-[1,2-b]-thiazole (18)

Compound (17) (410 mg; 1.20 mmol) was dissolved in 30 mL of methylene chloride and 4 mL of thionyl chloride was added with strong vortex at room temperature. After 15 minutes a solution made of 5.0 g of sodium carbonate in 50 mL of water was added. The mixture was refluxed for one hour at 65° C. The mixture was cooled down to room temperature and 100 mL of water and 100 mL of methylene chloride were added to the solution. The organic phase was extracted and washed with 3 times 100 mL of hydrochloric acid 10% in water. The acidic fractions were collected and brought to basic pH using ammonia. Product was extracted using methylene chloride. The organic phase was then dried using sodium sulfate and concentrated to yield a solid. This solid was then dissolved in acetone and a precipitate was obtained by addition of a 5% solution of hydrochloric acid in water. Precipitate was collected to yield 137 mg of white crystals (36%). MS m/z: 280 (M$^+$). NMR $^1$H (DMSO-D6) δ:3.69 (1H, m); 3.80 (2H, m); 4.00 (2H, t); 4.28 (1H, t); 5.80 (1H, m); from 7.40 to 7.79 (9H, m).

Example 4

Human intestinal AP was obtained from Aalto Scientific, Ltd. Vista, Calif. Human placental AP, bovine serum albumin, levamisole, and p-nitrophenyl phosphate {di(2-amino-2-ethyl-1,3-propanediol) salt} (PNPP) were obtained from Sigma Chemical Co., St. Louis, Mo. L-Phenylalanine was obtained from Aldrich Chemical Company, Milwaukee, Wis. Human bone AP was isolated from human osteosarcoma-derived cell line, Saos-2 (Catalog No. HTB 85, The American Type Culture Collection, 12301 Parklawn Drive, Rockville, Md.) by butanol extraction as described by J. R. Farley et al., (1989) *Clin Chem.* 35, 223–229.

*E. coli* AP (APKJ3 and APKJ4) were obtained according to the methods disclosed in U.S. patent Ser. No. 08/031,165 and its CIP. APKJ4 is an *E. coli* AP in which the lysine at its position 177 has been replaced with cysteine.

Compounds API-1, API-2 and API-3 were synthesized as shown in Examples 1,2 and 3, respectively.

AP activity was determined with VP Bichromatic Analyzer (Abbott Laboratories) by monitoring the appearance of the yellow product, p-nitrophenol, produced as a result of the enzyme catalyzed hydrolysis of the colorless substrate, p-nitrophenylphosphate. The stock preparations of *E. coli* and human AP were diluted to 0.3–1.0 U/ml with 0.1M Tris buffer, pH 8.0, containing 1 mM magnesium chloride, 0.1 mM zinc chloride and 5 mg/ml bovine serum albumin. Bovine serum albumin has been shown to stabilize the AP without contributing any phosphatase activity {Nigam, V. N. et al. (1959) *J. Biol. Chem.* 234, 1550; Nigam, V. N. et al. (1959) *J. Biol Chem.* 234, 2394}. The diluted enzyme solutions were prepared fresh just before the start of the experiments. The final assay conditions for the human and *E. coli* AP were as follows:

Human AP Isoenzymes: p-Nitrophenylphosphate (2.2 mmol/liter); Diethanolamine (500 mmol/liter); Magnesium chloride (1 mmol/liter); Zinc chloride (0.1 mmol/liter). The reaction pH was 10.2 at a reaction temperature of 37° C. and volume fraction (sample/total) of 0.033 (1:30).

*E. coli* AP: P-Nitrophenylphosphate (1 mmol/liter); Trischloride (100 mmol/liter); Magnesium chloride (1 mmol/liter); and Zinc chloride (0.1 mmol/liter). The reaction pH was 8.0 at a reaction temperature of 37° C. and volume fraction (sample/total) of 0.033 (1:30).

The diluted enzymes and inhibitors at appropriate concentrations (as shown in the Figures) were hand pipetted into numbered cuvettes in the multicuvette assembly of the VP Bichromatic Analyzer. Once the assay was started, the analyzer dispensed an appropriate amount of the buffered solution of p-nitrophenylphosphate containing magnesium and zinc chlorides into each cuvette. The multicuvette assembly rotated and allowed measurement of absorbance changes at every two minutes intervals. A 415 nm–450 nm filter was used to assay AP activity. All enzyme activity measurements were done at least in duplicate and the average value was used in the data analyses.

Figure 4:
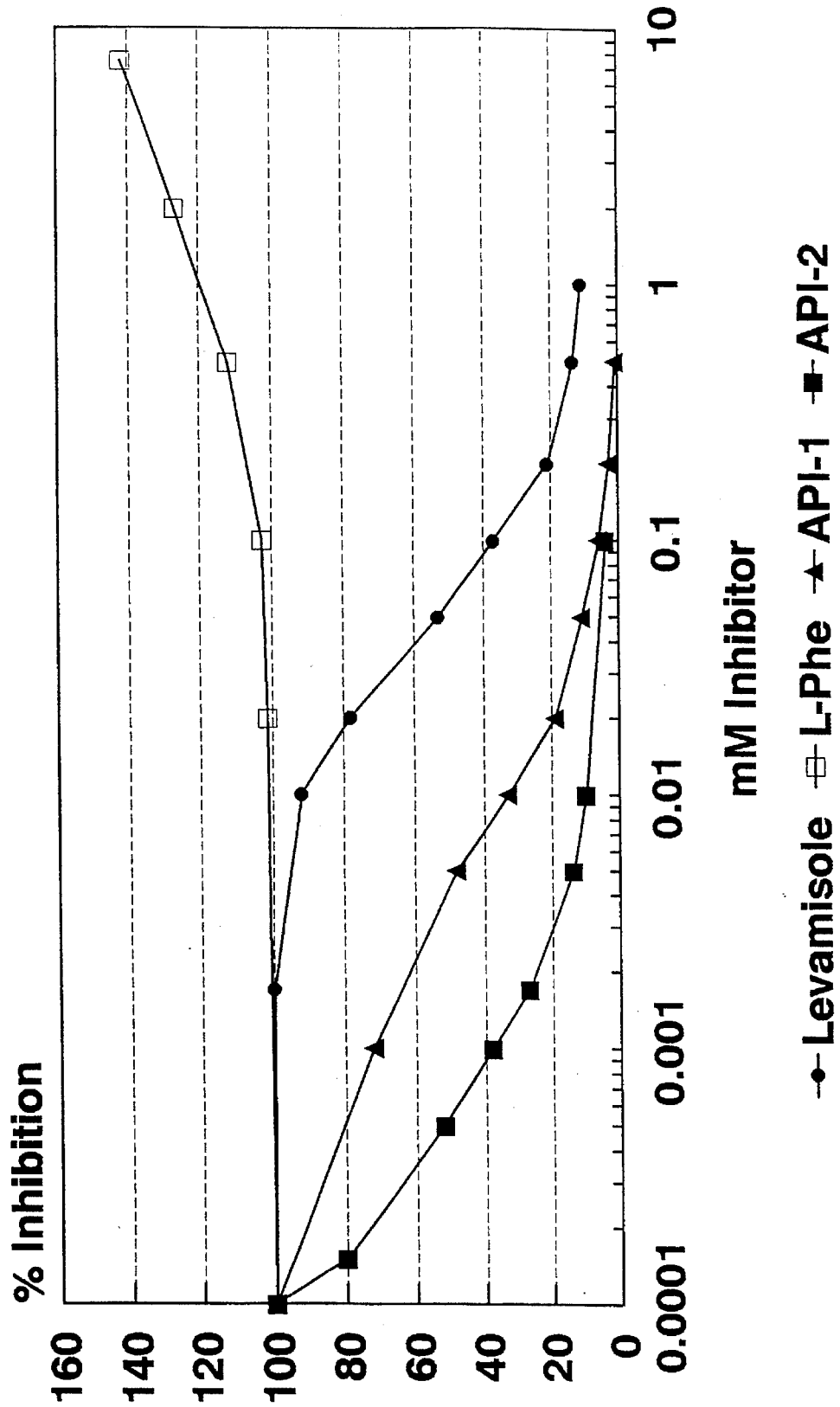
FIG. 4 compares the inhibition of human bone AP by levamisole, L-phenylalanine ("L-Phe"), novel compounds API-1 and API-2.

In order to characterize compounds API-1, API-3, and API-2 as inhibitors of human AP, inhibition of all the three types of isoenzymes, i.e. placental, intestinal, and bone (tissue-nonspecific) isoenzymes, by these compounds as well as by levamisole and L-phenylalanine was studied. FIG. 4 shows the data obtained with human bone AP isoenzymes. The inhibition data has been plotted as percent initial activity against inhibitor concentration.

L-phenylalanine does not inhibit bone isoenzymes. In fact, at higher concentrations, it activates the enzyme. As much as 40% increase in activity is observed at 10 mM concentration.

Compounds API-1 and API-2 strongly inhibit the bone isoenzymes, resulting in nearly complete inhibition at much lower concentrations compared to levamisole. The order of potency of these compounds as inhibitors of the bone AP was determined to be: API-2>API-1>levamisole.

Figure 5:
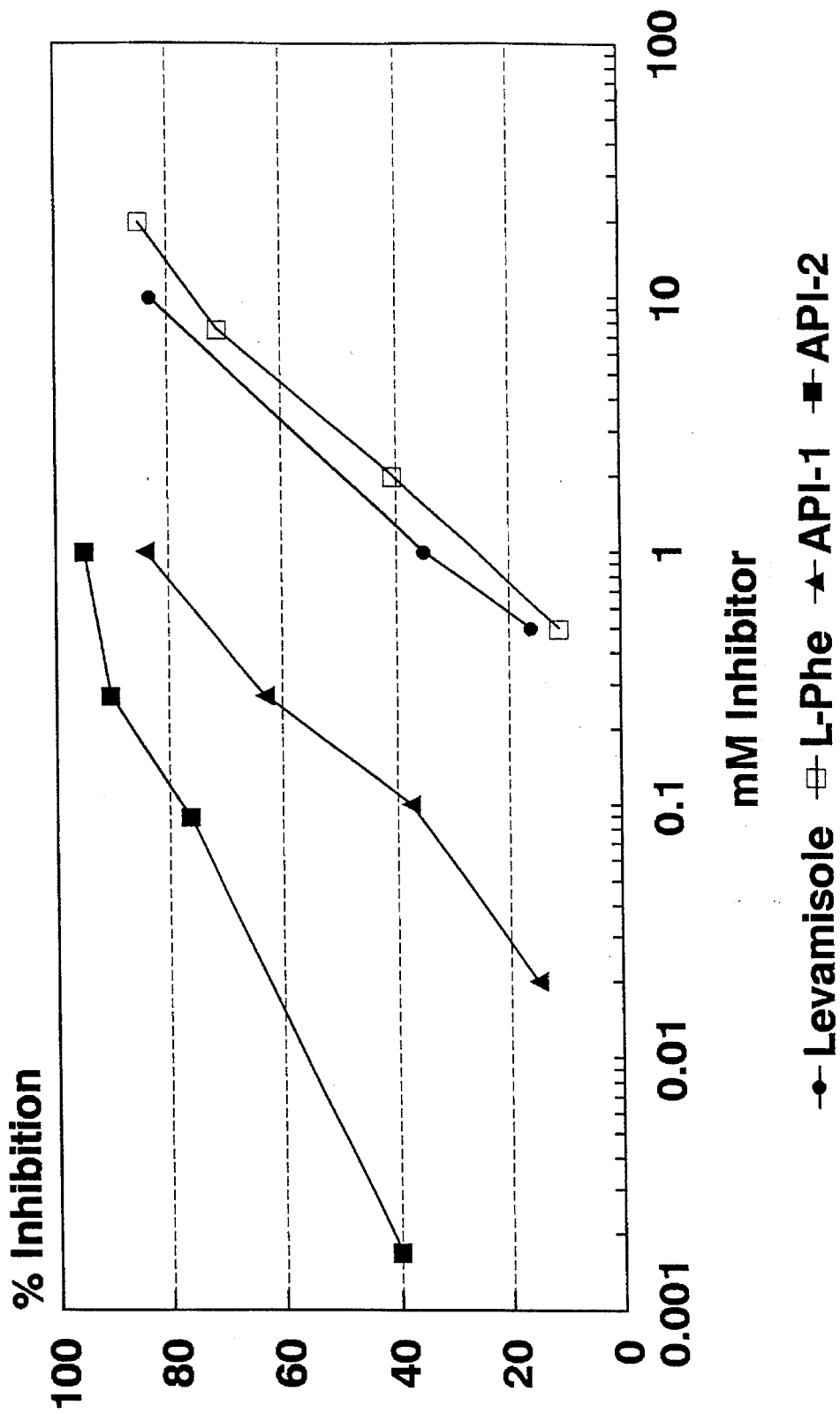
FIG. 5 compares the inhibition of human placental AP by levamisole, L-Phe, novel compounds API-1 and API-2.

The inhibition of the placental isoenzymes is shown in FIG. 5. L-phenylalanine and levamisole are quite comparable in their effectiveness as inhibitors of placental isoenzymes but both are a lot less effective compared to compounds API-1 and API-2. The order of effectiveness was API-2>API-1>levamisole>L-phenylalanine, as observed for the bone isoenzymes.

Figure 6:
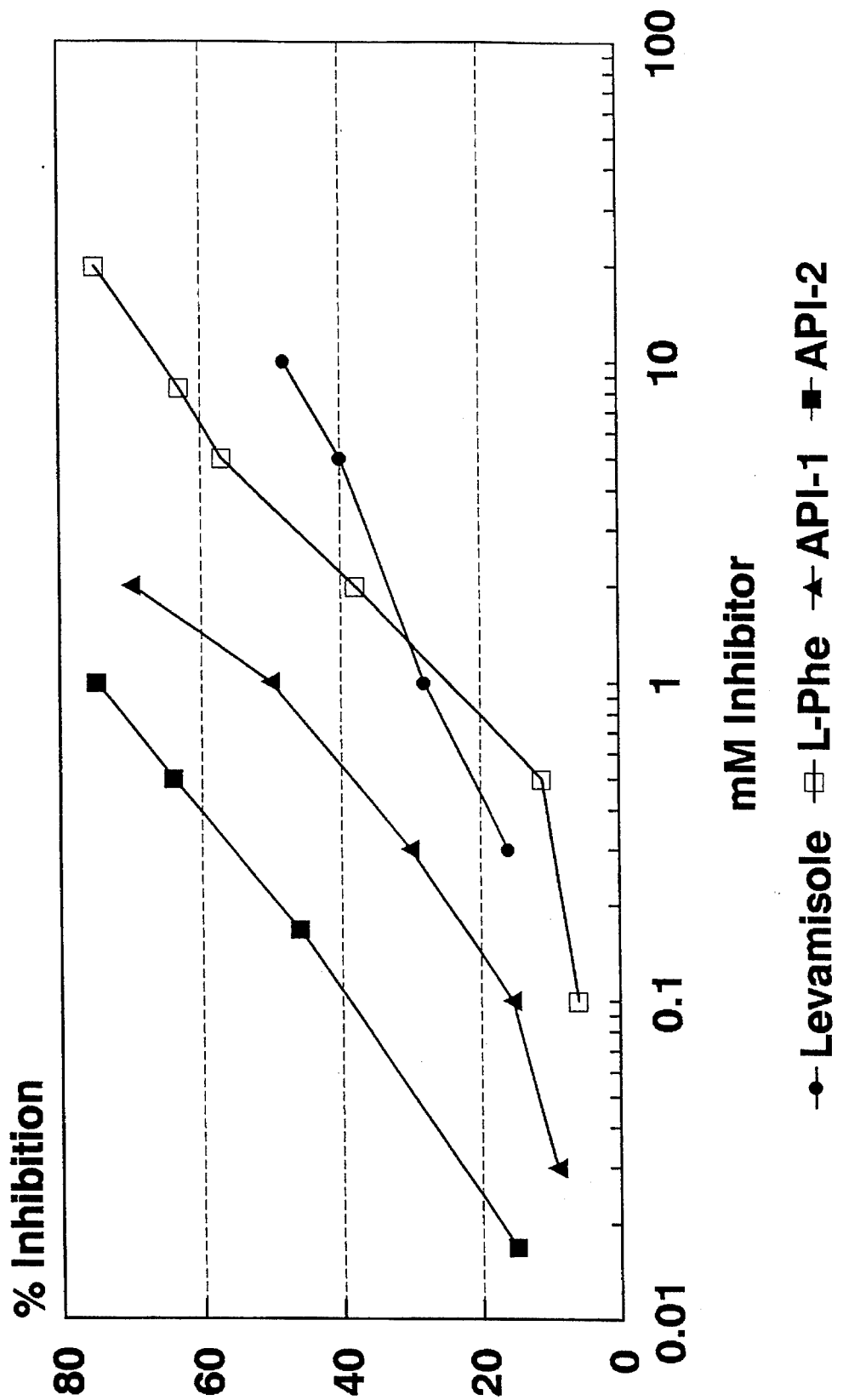
FIG. 6 compares the inhibition of human intestinal AP by levamisole, L-Phe, novel compounds API-1 and API-2.

FIG. 6 shows inhibition of the intestinal isoenzymes and once again compounds API-1 and API-2 were much more effective inhibitors than levamisole and L-phenylalanine. The order of effectiveness was API-2>API-1>L-phenylalanine>levamisole.

The $I_{50}$ values, the concentration of inhibitor that causes 50% inhibition, calculated from the dose response curves shown in FIGS. 4–6 for compounds API-1, API-2, levamisole, and L-phenylalanine are listed in Table 1 below. The $I_{50}$ value for API-3 is similarly calculated from its dose response curve.

TABLE 1

|  | $[I]_{50}$, mM | | |
|---|---|---|---|
|  | Bone AP | Placental AP | Intestinal AP |
| Levamisole | 0.06 | 2.20 | 12.0 |
| L—Phe | Activation | 3.00 | 4.50 |
| API-1 | 0.004 | 0.16 | 1.00 |
| API-2 | 0.0006 | 0.026 | 0.20 |
| API-3 | ND | 0.50 | ND |

$[I]_{50}$ = Concentration of Inhibitor that gives 50% inhibition of enzyme activity.
L—Phe = L-phenylalanine
ND = Not determined With respect to the bone isoenzymes, compounds API-1 is 15 times and API-2 is 100 times more active than levamisole.

With respect to the placental isoenzymes, API-1 is 14 and 19 times more potent than levamisole and L-phenylalanine, respectively. Compound API-2, on the other hand, is about 6 times more potent than compound API-1 and 85 and 115 times more potent than levamisole and L-phenylalanine, respectively.

With respect to inhibition of the intestinal isoenzymes, API-1 is 5 and 12 times as potent as L-phenylalanine and levamisole, respectively, whereas compound API-2 is 5 times as effective as API-1 and 23 and 60 times as effective as L-phenylalanine and levamisole, respectively. Table 1 also shows that among the isoenzymes tested, human intestinal AP is the most resistant to inhibition by the compounds tested.

Figure 7:
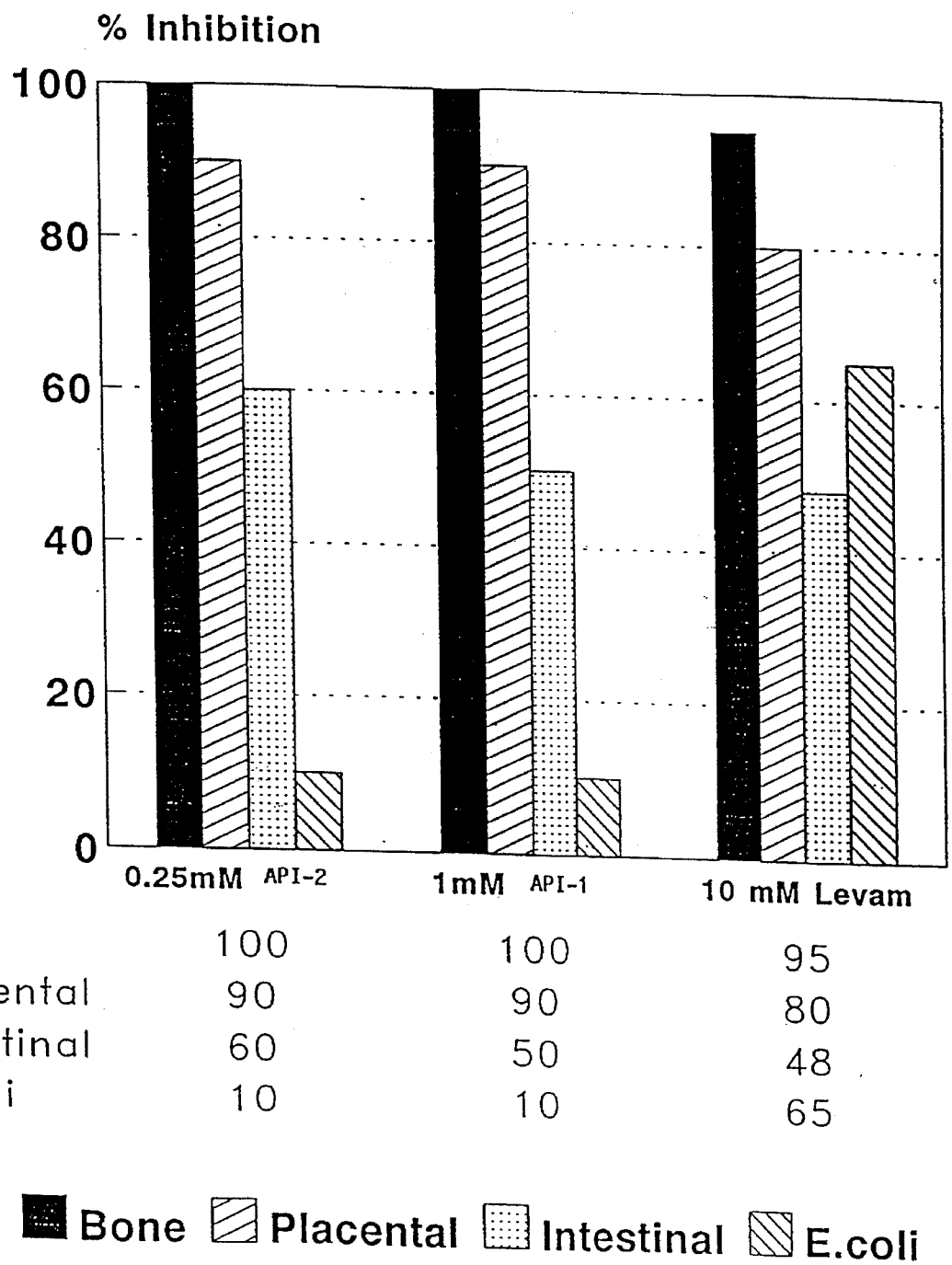
FIG. 7 compares the selectivity of novel compounds API-2, API-1, and levamisole ("Levam") for *E. coli* AP and AP from human bone, placental, and intestinal sources.

API-1 and API-2 are also much more selective inhibitors of human AP compared to levamisole as illustrated in FIG. 7. At concentrations that show complete inhibition of the bone isoenzymes, 90% inhibition of the placental isoenzymes, and 50–60% inhibition of the intestinal isoenzymes, compounds API-1 and API-2 cause only 10% or less inhibition of the *E. coli* AP. In contrast, at concentration that shows 95% inhibition of the bone isoenzymes, 80% inhibition of the placental isoenzymes, and only 48% inhibition of the intestinal isoenzymes, levamisole also causes 65% inhibition of the *E. coli* AP.

The above experiment was repeated using calf intestinal AP and it was found that API-1 and API-2 inhibited calf intestinal AP more than *E. coli* AP. Additionally, it was found that API-1 and API-2 are more effective in inhibiting human intestinal AP than calf intestinal AP. They were also more efficient than L-phenylalanine and levamisole at inhibiting calf intestinal AP.

The invention described herein draws on both published and unpublished work. By way of example, such work consists of scientific papers, pending patent applications, and patents. All of the works cited in this application are hereby incorporated by reference in their entirety.

The foregoing description of the presently preferred embodiments of the present invention has been offered for purposes of illustration and description. It is not intended to limit the scope of the invention, which is defined by the appended claims and their equivalents. Various modifications and variations of the preferred embodiments are possible in light of the above teachings and will be apparent to persons skilled in the art. Such modifications and variations do not depart from the spirit or scope of the invention and it is therefore intended that the scope of the invention be defined by the appended claims, including all equivalents.

We claim:

1. A compound selected from the group consisting of: General Formula 1, General Formula 2, and a salt of General Formula 1 or 2; wherein General Formulae 1 and 2 are as follow:

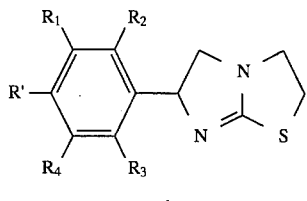

General Formula 1 and

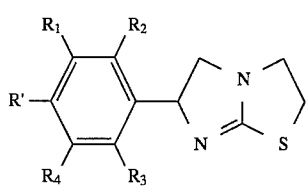

General Formula 2 wherein:

R' is selected from the group consisting of: aryl, aryl ether, aryl thioether, aromatic heterocyclic, aromatic heterocyclic thioether, and aromatic heterocyclic ether groups;

$R_1$, $R_2$, $R_3$ and $R_4$ are the same or different wherein $R_1$, $R_2$, $R_3$ and $R_4$ are selected from the group consisting of H, $C_1$–$C_6$ alkyl, halo $C_1$–$C_6$ alkyl, phenyl, $C_1$–$C_6$ alkoxy, phenoxy, trifluoromethyl, nitro, amino, carboxy, and halo groups, with the proviso that the compound has no more than three substituents; and R', $R_1$, $R_2$, $R_3$ and $R_4$ do not significantly prevent the compound from binding to and inhibiting the enzymatic activity of alkaline phosphatase.

2. The compound of claim 1, wherein the compound inhibits the enzymatic activity of mammalian alkaline phosphatase more than the enzymatic activity of non-mammalian alkaline phosphatase.

3. The compound of claim 2, wherein the non-mammalian alkaline phosphatase is *E. coli* alkaline phosphatase.

4. The compound of claim 2, wherein the mammalian alkaline phosphatase is human or calf alkaline phosphatase.

5. The compound of claim 4, wherein the non-mammalian alkaline phosphatase is *E. coli* alkaline phosphatase.

6. The compound of claim 1, wherein $R_1$, $R_2$, $R_3$, or $R_4$ are selected from the group consisting of $C_1$–$C_4$ alkyl, $C_1$–$C_4$ alkoxy, bromide, chloride, fluoride, phenoxy, phenyl, trifluoromethyl, nitro, primary amine, carboxylic acid, and hydrogen, with the proviso that the compound has no more than three substituents.

7. The compound of claim 6, wherein $R_1$, $R_2$, $R_3$, or $R_4$ are selected from the group consisting of methyl, methoxy, nitro, primary amine, chloride, and hydrogen.

8. The compound of claim 7, wherein $R_1$, $R_2$, $R_3$, and $R_4$ are hydrogen.

9. The compound of claim 1, wherein R' is a phenyl or a pyridine.

10. The compound of claim 9, wherein the compound inhibits the enzymatic activity of mammalian alkaline phosphatase more than the enzymatic activity of non-mammalian alkaline phosphatase.

11. The compound of claim 10, wherein the non-mammalian alkaline phosphatase is *E. coli* alkaline phosphatase.

12. The compound of claim 10, wherein the mammalian alkaline phosphatase is human or calf alkaline phosphatase.

13. The compound of claim 12, wherein the non-mammalian alkaline phosphatase is *E. coli* alkaline phosphatase.

14. The compound of claim 9, wherein R' is selected from the group consisting of

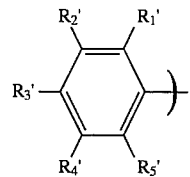

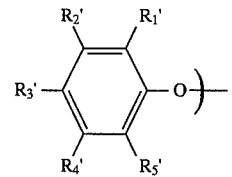

and

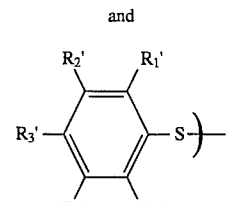

wherein $R_1$, $R_2$, $R_3$, $R_4$, $R_1'$, $R_2'$, $R_3'$, $R_4'$, and $R_5'$ are the same or different wherein $R_1'$, $R_2'$, $R_3'$, $R_4'$ and $R_5'$ are selected from the group consisting of H, $C_1$–$C_6$ alkyl, halo $C_1$–$C_6$ alkyl, phenyl, $C_1$–$C_6$ alkoxy, phenoxy, trifluoromethyl, nitro, amino, carboxy, and halo groups with the proviso that the compound has more than three substituents.

15. The compound of claim 14, wherein $R_1$, $R_2$, $R_3$, $R_4$, $R_1'$, $R_2'$, $R_3'$, $R_4'$, and $R_5'$ are selected from the group consisting of $C_1$–$C_4$ alkyl, $C_1$–$C_4$ alkoxy, bromide, chloride, fluoride, phenoxy, phenyl, trifluoromethyl, nitro, primary amine, carboxylic acid, and hydrogen with the proviso that the compound has no more than three substituents.

16. The compound of claim 15, wherein $R_1$, $R_2$, $R_3$, $R_4$, $R_1'$, $R_2'$, $R_3'$, $R_4'$, and $R_5'$ are selected from the group consisting of methyl, methoxy, nitro, primary amine, chloride, and hydrogen.

17. The compound of claim 16, wherein $R_1$ to $R_4$ and $R_1'$ to $R_5'$ are hydrogen.

18. The compound of claim 15, wherein the compound inhibits the enzymatic activity of mammalian alkaline phosphatase more than the enzymatic activity of non-mammalian alkaline phosphatase.

19. The compound of claim 18, wherein the non-mammalian alkaline phosphatase is *E. coli* alkaline phosphatase.

20. The compound of claim 19, wherein the mammalian alkaline phosphatase is human or calf alkaline phosphatase.

21. The compound of claim 9, wherein R' is

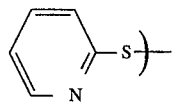

2-thiopyridine, or

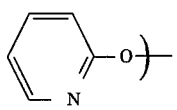

2-oxypyridine.

22. The compound of claim 21, wherein $R_1$, $R_2$, $R_3$, or $R_4$ are selected from the group consisting of H, $C_1$–$C_6$ alkyl, halo $C_1$–$C_6$ alkyl, phenyl, $C_1$–$C_6$ alkoxy, phenoxy, trifluoromethyl, nitro, amino, carboxy, and halo groups, with the proviso that the compound has no more than three substituents.

23. The compound of claim 21, wherein $R_1$, $R_2$, $R_3$, or $R_4$ are selected from the group consisting of $C_1$–$C_4$ alkyl, $C_1$–$C_4$ alkoxy, bromide, chloride, fluoride, phenoxy, phenyl, trifluoromethyl, nitro, primary amine, carboxylic acid, and hydrogen, with the proviso that the compound has no more than three substituents.

24. The compound of claim 21, wherein $R_1$, $R_2$, $R_3$, or $R_4$ are selected from the group consisting of methyl, methoxy, nitro, primary amine, chloride, and hydrogen.

25. The compound of claim 21, wherein $R_1$, $R_2$, $R_3$, and $R_4$ are hydrogen.

26. The compound of claim 1, selected from the group consisting of (dl)-2,3,5,6-tetrahydro-6-(4-phenoxyphenyl)-imidazo[2,1-b]-thiazole, (dl)-5,6-dihydro-6-(4-phenoxyphenyl)-imidazo-[1,2-b]-thiazole; and (dl)-2,3,5,6-tetrahydro-6-(biphenyl)-imidazo-[1,2-b]-thiazole.

27. The compound of claim 20, wherein the non-mammalian alkaline phosphatase is *E. coli* alkaline phosphatase.

28. An assay for an analyte in a sample, wherein the sample is believed likely to contain mammalian alkaline phosphatase, comprising the steps of:

a) exposing the sample to a solid support capable of binding the analyte and mammalian alkaline phosphatase;

b) incubating the sample and the solid support for a time sufficient for the binding of the analyte to the solid support;

c) removing reagents which are not bound to the solid support;

d) exposing the solid support to a reagent capable of binding to the analyte, the reagent being labeled with non-mammalian alkaline phosphatase;

e) incubating the solid support and the reagent for a time sufficient for the binding of the reagent to the analyte which is bound to the solid support;

f) removing the reagent which is not bound to the solid support bound analyte;

g) adding a compound and a substrate for alkaline phosphatase to the solid support; and h) assaying for the presence of the analyte by assaying for the conversion of the substrate into an enzymatic product of the non-mammalian alkaline phosphatase;

wherein the compound has the formula selected from the group consisting of General Formula 1, General Formula 2, and a salt of General Formulae 1 and 2; wherein General Formulae 1 and 2 are as follow:

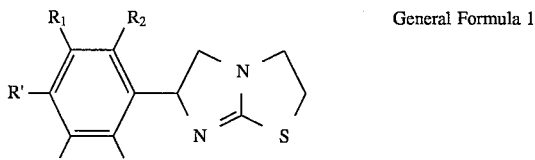

General Formula 1 and

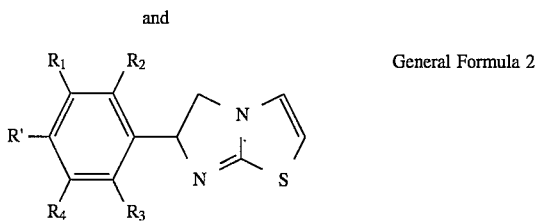

General Formula 2 wherein:

R' is selected from the group consisting of: aryl, aryl ether, aryl thioether, aromatic heterocyclic, aromatic heterocyclic thioether, and aromatic heterocyclic ether groups;

$R_1$, $R_2$, $R_3$ and $R_4$ are the same or different wherein $R_1$, $R_2$, $R_3$ and $R_4$ are selected from the group consisting of H, $C_1$–$C_6$ alkyl, halo $C_1$–$C_6$ alkyl, phenyl, $C_1$–$C_6$ alkoxy, phenoxy, trifluoromethyl, nitro, amino, carboxy, and halo groups, with the proviso that the compound has no more than three substituents; and R', $R_1$, $R_2$, $R_3$ and $R_4$ do not significantly prevent the novel compound from binding to and inhibiting the enzymatic activity of mammalian alkaline phosphatase more than inhibiting the enzymatic activity of non-mammalian alkaline phosphatase.

29. A method for determining the presence or amount of an analyte in a test sample, wherein the test sample may contain mammalian alkaline phosphatase, comprising the steps of:

a) sequentially or simultaneously allowing the test sample, a binding molecule of the analyte, a non-mammalian alkaline phosphatase, alkaline phosphatase substrate, and a compound to come into contact; and b) monitoring changes in the rate of catalysis of the alkaline phosphatase substrate by the non-mammalian alkaline phosphatase, the changes being dependent upon the analyte present in the reaction mixture; wherein:

the non-mammalian alkaline phosphatase and the analyte compete for binding to the binding molecule;

the enzymatic activity of the non-mammalian alkaline phosphatase is when it is bound to the binding molecule, the compound has a formula selected from the group consisting of: General Formula 1, General Formula 2, and a salt of General Formulae 1 and 2; wherein General Formulae 1 and 2 are as follow:

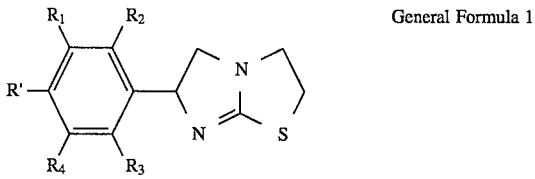

General Formula 1

-continued

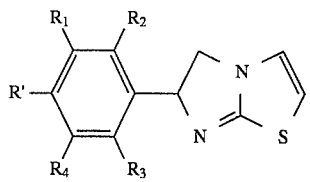

General Formula 2 wherein:

R' is selected from the group consisting of: aryl, aryl ether, aryl thioether, aromatic heterocyclic, aromatic heterocyclic thioether, and aromatic heterocyclic ether groups;

$R_1$, $R_2$, $R_3$ and $R_4$ are the same or different wherein $R_1$, $R_2$, $R_3$ and $R_4$ are selected from the group consisting of H, $C_1$–$C_6$ alkyl, halo $C_1$–$C_6$ alkyl, phenyl, $C_1$–$C_6$ alkoxy, phenoxy, trifluoromethyl, nitro, amino, carboxy, and halo groups, with the proviso that the compound has no ore than three substituents; and R', $R_1$, $R_2$, $R_3$ and $R_4$ do not significantly prevent the compound from binding to and inhibiting the enzymatic activity of mammalian alkaline phosphatase more than inhibiting the enzymatic activity of non-mammalian alkaline phosphatase.

30. The method of claim 29, wherein the non-mammalian alkaline phosphatase is a bacterial alkaline phosphatase which has been genetically altered, such that (a) an epitope for the binding molecule has been created on the bacterial alkaline phosphatase, or (b) a binding site for a ligand has been created on the bacterial alkaline phosphatase, the ligand is bound to the binding site, and the binding molecule is capable of binding to the bound ligand.

31. The method of claim 30, wherein the bacterial alkaline phosphatase is *E. coli* alkaline phosphatase.

32. A test kit comprising:

(a) a first container containing a substrate for alkaline phosphatase; and (b) a second container containing a compound selected from the group consisting of General Formula 1, General Formula 2, and a salt of General Formula 1 or 2; wherein General Formulae 1 and 2 are as follow:

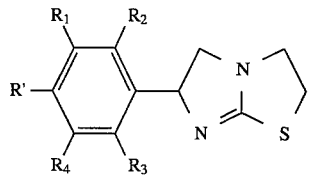

General Formula 1 and

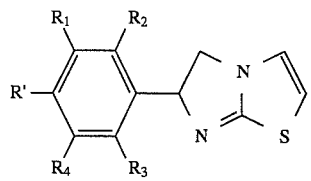

General Formula 2 wherein:

R' is selected from the group consisting of: aryl, aryl ether, aryl thioether, aromatic heterocyclic, aromatic heterocyclic thioether, and aromatic heterocyclic ether groups;

$R_1$, $R_2$, $R_3$ and $R_4$ are the same or different wherein $R_1$, $R_2$, $R_3$ and $R_4$ are selected from the group consisting of H, $C_1$–$C_6$ alkyl, halo $C_1$–$C_6$ alkyl, phenyl, $C_1$–$C_6$ alkoxy, phenoxy, trifluoromethyl, nitro amino, carboxy, and halo groups, with the proviso that the compound has no more than three substituents; and R', $R_1$, $R_2$, $R_3$ and $R_4$ do not significantly prevent the compound from binding to and inhibiting the enzymatic activity of alkaline phosphatase.

33. A test kit comprising:

(a) a first container containing at least one of the following: a non-mammalian alkaline phosphatase and a binding molecule; and (b) a second container containing a compound selected from the group consisting of General Formula 1, General Formula 2, and a salt of General Formula 1 or 2; wherein General Formulae 1 and 2 are as follow:

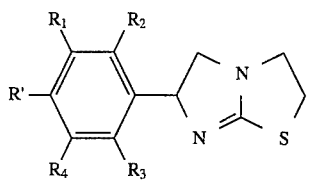

General Formula 1 and

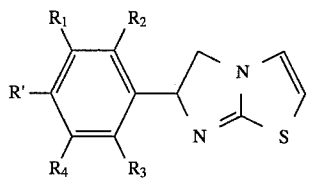

General Formula 2 wherein:

R' is selected from the group consisting of aryl, aryl ether, aryl thioether, aromatic heterocyclic, aromatic heterocyclic thioether, and aromatic heterocyclic ether groups;

$R_1$, $R_2$, $R_3$ and $R_4$ are the same or different wherein $R_1$, $R_2$, $R_3$ and $R_4$ are selected from the group consisting of H, $C_1$–$C_6$ alkyl, halo $C_1$–$C_6$ alkyl, phenyl, $C_1$–$C_6$ alkoxy, phenoxy, trifluoromethyl, nitro, amino, carboxy, and halo groups, with the proviso that the compound has no more than three substituents;

R', $R_1$, $R_2$, $R_3$ and $R_4$ do not significantly prevent the compound from binding to and inhibiting the enzymatic activity of mammalian alkaline phosphatase;

the non-mammalian alkaline phosphatase and the analyte compete for binding to the binding molecule; and the enzymatic activity of the non-mammalian alkaline phosphatase is when it is bound to the binding molecule.

34. A test kit comprising:

(a) a first container containing a detection reagent labeled with a non-mammalian alkaline phosphatase, and (b) a second container containing a compound;

wherein the compound has a formula selected from the group consisting of General Formula 1, General Formula 2, and a salt of General Formulae 1 and 2; wherein General Formulae 1 and 2 are as follow:

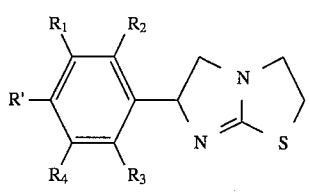 General Formula 1 and

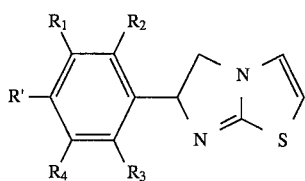 General Formula 2 wherein:

R' is selected from the group consisting of: aryl, aryl ether, aryl thioether, aromatic heterocyclic, aromatic heterocyclic thioether, and aromatic heterocyclic ether groups;

$R_1$, $R_2$, $R_3$ and $R_4$ are the same or different wherein $R_1$, $R_2$, $R_3$ and $R_4$ are selected from the group consisting of H, $C_1$–$C_6$ alkyl, halo $C_1$–$C_6$ alkyl, phenyl, $C_1$–$C_6$ alkoxy, phenoxy, trifluoromethyl, nitro, amino, carboxy, and halo groups, with the proviso that the compound has no more than three substituents; and R', $R_1$, $R_2$, $R_3$ and $R_4$ do not significantly prevent the compound from binding to and inhibiting the enzymatic activity of mammalian alkaline phosphatase.

\* \* \* \* \*

UNITED STATES PATENT AND TRADEMARK OFFICE
CERTIFICATE OF CORRECTION

PATENT NO. : 5,516,647
DATED : May 14, 1996
INVENTOR(S) : M. Husain, et. Al.

It is certified that error appears in the above-indentified patent and that said Letters Patent is hereby corrected as shown below:

On the title page, item[75]:
In the list of inventors, please delete "Christopher Bieniarz, Highland Park".

Column 2, line 24, change "Sic U.S.A." to --Sci. U.S.A.--.

Column 2, line 26, change "Sic U.S.A." to --Sci. U.S.A.--.

Column 2, line 27, change "Sic U.S.A." to --Sci. U.S.A.--.

Column 2, line 29, change "Sic U.S.A." to --Sci. U.S.A.--.

Column 4, line 60, change "2-thiopyridine" to --(2-thiopyridine--.

Column 4, line 67, change "2-oxypyridine" to --(2-oxypyridine--.

Column 5, line 2, change "tile" to --the--.

Column 6, line 15, change "API-1" to --API-1--.

Column 6, line 28, change "API-2" to --API-2--.

Column 6, line 40, change "API-3" to --API-3--.

Column 7, line 52, change "isoenzymes" to --isoenzyme--.

Column 8, line 51, change "i is" to --it is--.

Column 12, lines 22-23, change "$1 \times 10^-{}_6 M$" to --$1 \times 10^{-6} M$--.

Column 15, lines 35-36, change "Nematospiroides" to --Nematospiroides--.

Column 15, line 48, change "a" to --as--.

UNITED STATES PATENT AND TRADEMARK OFFICE
CERTIFICATE OF CORRECTION

PATENT NO. : 5,516,647
DATED : May 14, 1996
INVENTOR(S) : M. Husain, et. Al.

It is certified that error appears in the above-indentified patent and that said Letters Patent is hereby corrected as shown below:

Column 15, line 51, change "s as" to --as--.

Column 18, line 41, change "Gr" to --Gr- --.

Column 19, line 54, change "DMSOD" to --DMSO--.

Column 21, lines 47-48, change "(1H, m); J=6Hz);" to --(1H, d, J=6Hz);--.

Column 22, line 22, change "(2:H,s)" to --(2H,s)--.

Column 24, line 25, change "APl" to --APl--.

Column 24, line 26, change "APl" to --APl--.

Column 24, line 27, change "APl" to --Apl--.

Column 25, line 17, change "of;" to --of--.

Column 25, line 39, change "of:" to --of--.

Column 27, line 10, change "2-thiopyridine" to --(2-thiopyridine)--.

Column 27, line 16, change "2-oxypyridine" to --(2-oxypyridine)--.

Column 27, line 17, change "or" to --and--.

Column 27, line 23, change "or" to --and--.

Column 27, line 29, change "or" to --and--.

Column 28, line 37, change "may" to --is believed likely to--.

UNITED STATES PATENT AND TRADEMARK OFFICE
CERTIFICATE OF CORRECTION

PATENT NO. : 5,516,647  
DATED : May 14, 1996  
INVENTOR(S) : M. Husain, et. Al.

It is certified that error appears in the above-indentified patent and that said Letters Patent is hereby corrected as shown below:

Column 28, line 56, change "of:" to --of--.

Column 29, line 21, change "ore" to --more--.

Column 30, line 2, change "nitro amino" to --nitro, amino--.

Signed and Sealed this

Eleventh Day of March, 1997

Attest:

BRUCE LEHMAN

*Attesting Officer*      *Commissioner of Patents and Trademarks*